United States Patent
Sasai et al.

(10) Patent No.: US 11,274,277 B2
(45) Date of Patent: Mar. 15, 2022

(54) METHOD FOR PRODUCING ANTERIOR EYE SEGMENT TISSUE

(71) Applicants: RIKEN, Wako (JP); Sumitomo Chemical Company, Limited, Tokyo (JP)

(72) Inventors: Yoshiki Sasai, Kobe (JP); Chikafumi Ozone, Wako (JP); Yuko Maruyama, Wako (JP)

(73) Assignees: RIKEN, Wako (JP); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/910,332

(22) PCT Filed: Aug. 6, 2014

(86) PCT No.: PCT/JP2014/070748
§ 371 (c)(1),
(2) Date: Feb. 5, 2016

(87) PCT Pub. No.: WO2015/020091
PCT Pub. Date: Feb. 12, 2015

(65) Prior Publication Data
US 2016/0186136 A1    Jun. 30, 2016

(30) Foreign Application Priority Data
Aug. 6, 2013 (JP) ............................. JP2013-163586

(51) Int. Cl.
*C12N 5/079* (2010.01)

(52) U.S. Cl.
CPC ........ *C12N 5/0621* (2013.01); *C12N 2500/90* (2013.01); *C12N 2501/115* (2013.01);
(Continued)

(58) Field of Classification Search
CPC ............ C12N 5/0621; C12N 2501/155; C12N 2500/90
See application file for complete search history.

(56) References Cited

U.S. PATENT DOCUMENTS

| | | |
|---|---|---|
| 6,030,794 A | 2/2000 | Chambon et al. |
| 8,956,866 B2 | 2/2015 | Idelson et al. |

(Continued)

FOREIGN PATENT DOCUMENTS

| | | |
|---|---|---|
| EP | 1598417 A1 | 11/2005 |
| EP | 1616941 A1 | 1/2006 |

(Continued)

OTHER PUBLICATIONS

Bratt-Leal et al., Biomater., 34(30):7227-7235 (2013).*
(Continued)

*Primary Examiner* — David W Berke-Schlessel
*Assistant Examiner* — Trent R Clarke
(74) *Attorney, Agent, or Firm* — Leydig, Voit & Mayer, Ltd.

(57) ABSTRACT

The present invention provides a production method of a cell aggregate containing an anterior eye segment tissue or a partial structure thereof, or a precursor tissue thereof, including culturing pluripotent stem cell aggregates in suspension in the presence of a bone morphogenic factor signal transduction pathway activating substance to induce self-organization of an anterior eye segment tissue or a partial structure thereof, or a precursor tissue thereof. In one embodiment, the bone morphogenic factor signal transduction pathway activating substance is BMP4. In one embodiment, the suspension culture is performed entirely or partially in the presence of a fibroblast growth factor. The produced cell aggregate can further contain a neural retinal tissue.

17 Claims, 8 Drawing Sheets

(52) U.S. Cl.
CPC .. *C12N 2501/155* (2013.01); *C12N 2501/727* (2013.01); *C12N 2506/02* (2013.01)

(56) References Cited

U.S. PATENT DOCUMENTS

| | | | |
|---|---|---|---|
| 2005/0232916 A1 | 10/2005 | Martin et al. | |
| 2007/0037282 A1* | 2/2007 | Takahashi | C12N 5/0621 435/368 |
| 2008/0124276 A1 | 5/2008 | Hammond et al. | |
| 2010/0068793 A1* | 3/2010 | Ungrin | B01L 3/5085 435/283.1 |
| 2011/0027333 A1 | 2/2011 | Idelson et al. | |
| 2011/0091869 A1* | 4/2011 | Sasai | C12N 5/0623 435/5 |
| 2012/0149598 A1 | 6/2012 | Inoue et al. | |
| 2012/0282318 A1 | 11/2012 | Nishida et al. | |
| 2013/0040330 A1 | 2/2013 | Sasai et al. | |
| 2013/0136721 A1* | 5/2013 | Zambidis | C12N 5/0657 424/93.7 |
| 2014/0308743 A1* | 10/2014 | Sasai | C12N 5/0616 435/373 |
| 2015/0118749 A1 | 4/2015 | Idelson et al. | |
| 2015/0125506 A1 | 5/2015 | Idelson et al. | |
| 2017/0065642 A1 | 3/2017 | Hammond et al. | |

FOREIGN PATENT DOCUMENTS

| | | | | |
|---|---|---|---|---|
| JP | H08-504104 A | 5/1996 | | |
| JP | 2005-534001 A | 11/2005 | | |
| JP | 2009-544313 A | 12/2009 | | |
| JP | 2010-524457 A | 7/2010 | | |
| WO | WO 2009/148170 A1 | 12/2009 | | |
| WO | WO 2010/084970 A1 | 7/2010 | | |
| WO | WO 2011/021706 A1 | 2/2011 | | |
| WO | WO 2011/055855 A1 | 5/2011 | | |
| WO | WO 2012/073238 A1 | 6/2012 | | |
| WO | WO 2013/065763 | * | 5/2013 | C12N 5/0735 |
| WO | WO 2013/065763 A1 | 5/2013 | | |
| WO | WO 2013/086236 A2 | 6/2013 | | |

OTHER PUBLICATIONS

Hayashi et al., PLoS ONE, 7(9):e45435, pp. 1-11 (2012).*
Eiraku et al., Nat. Protoc., (7)(1):69-79 (2012).*
Yoshida et al., Differentiation, 80(P82):S44-S45 (2010).*
Ikeda et al., PNAS, 102(32):11331-11336 (2005).*
Nakano et al., Cell Stem Cell, 10:771-785 (2012).*
Shalom-Feuerstein et al., Stem Cells, 30:898-909 (2012).*
Cvekl et al., Bioessays., 26(4): 374-386 (2004). (Year: 2004).*
Sjodal et al., Dev. Cell, 13:141-149 (2007) (Year: 2007).*
Behesti et al., BMC Develop. Biol., 6(62):1-22 (2006) (Year: 2006).*
Faber et al., Develop., 129:3727-3737 (2002) (Year: 2002).*
Furuta et al., Genes Develop., 12:3764-3775 (1998) (Year: 1998).*
Hamidabadi et al., Int. J. Fertil. Steril., 5(2):104-109 (2011) (Year: 2011).*
Ahmad et al., "Differentiation of Human Embryonic Stem Cells into Corneal Epithelial-Like Cells by In Vitro Replication of the Corneal Epithelial Stem Cell Niche," *Stem Cells*, 25(5): 1145-1155 (2007).
Chan et al., "Differentiation of Human Embryonic Stem Cells into Cells with Corneal Keratocyte Phenotype," *PLoS One*, 8(2): e56831 (2013).
Eiraku et al., "Self-organizing optic-cup morphogenesis in three-dimensional culture," *Nature*, 472(7341): 51-56 (2011).
Hayashi et al., "Generation of Corneal Epithelial Cells from Induced Pluripotent Stem Cells Derived from Human Dermal Fibroblast and Corneal Limbal Epithelium," *PLoS One*, 7(9): e45435 (2012).
Leenders et al., "Synergism between temporally distinct growth factors: bFGF, insulin and lens cell differentiation," *Mech. Dev.*, 67(2): 193-201 (1997).
Leung et al., "Differential BMP signaling controls formation and differentiation of multipotent preplacodal ectoderm progenitors from human embryonic stem cells," *Dev. Biol.*, 379(2): 208-220 (2013).
Metallo et al., "Retinoic Acid and Bone Morphogenetic Protein Signaling Synergize to Efficiently Direct Epithelial Differentiation of Human Embryonic Stem Cells," *Stem Cells*, 26(2): 372-380 (2008).
Nakano et al., "Self-Formation of Optic Cups and Storable Stratified Neural Retina from Human ESCs," *Cell Stem Cell*, 10(6): 771-785 (2012).
Wataya et al., "Minimization of exogenous signals in ES cell culture induces rostral hypothalamic differentiation," *Proc. Natl. Acad. Sci. U.S.A.*, 105(33): 11796-11801 (2008).
Yang et al., "Efficient generation of lens progenitor cells and lentoid bodies from human embryonic stem cells in chemically defined conditions," *FASEB J.*, 24(9): 3274-3283 (2010).
Yoshida et al., "Generation of Stratified Squamous Epithelial Progenitor Cells from Mouse Induced Pluripotent Stem Cells," *PLoS One*, 6(12): e28856 (2011).
Japanese Patent Office, International Search Report in International Patent Application No. PCT/JP2014/070748 (dated Nov. 11, 2014).
Eiraku et al., "Mouse embryonic stem cell culture for generation of three-dimensional retinal and cortical tissues," *Nat. Protocol.*, 7(1): 69-79 (2012).
Yoshida et al., "Differentiation of induced pluripotent stem cells into corneal epithelial cells," *Differentiation*, 80(Suppl. 1): S44-S45, Abstract No. P82 (2010).
Vrijens et al., "Identification of Small Molecule Activators of BMP Signaling," *PLoS One*, 8(3): e59045 (2013).

* cited by examiner

METHOD FOR PRODUCING ANTERIOR EYE SEGMENT TISSUE

CROSS-REFERENCE TO RELATED APPLICATIONS

This patent application is the U.S. national phase of International Patent Application No. PCT/JP2014/070748, filed Aug. 6, 2014, which claims the benefit of Japanese Patent Application No. 2013-163586, filed on Aug. 6, 2013, which are incorporated by reference in their entireties herein.

TECHNICAL FIELD

The present invention relates to a technique for inducing differentiation of a pluripotent stem cell into an anterior eye segment tissue in vitro.

BACKGROUND ART

The present inventors have heretofore succeeded, by using an SFEBq method (patent document 1), in developing retinal precursor tissues containing a neural retinal tissue and a retinal pigment epithelial tissue from pluripotent stem cells by culturing pluripotent stem cell aggregates in suspension in a serum-free medium, and forming an optic cup, which is the primordium of the eye, by self-organization in vitro (patent document 2, non-patent documents 1 and 2). However, induction of anterior eye segment tissues such as cornea, lens and the like, which constitute the eyeball together with the retina, from pluripotent stem cells by suspension culture in vitro has not been reported.

Non-patent document 3 reports induction of corneal epithelial cells by adhesion culture of human iPS cells on a PA6 feeder layer. However, culture in the presence of feeder cells is not preferable since contamination with undefined factors should be avoided. In addition, steric structures of cornea and the like have not been constructed. The method described in this document requires a long term of 12 weeks for the induction of corneal epithelial cells. This document also describes that a BMP4 treatment suppressed differentiation of iPS cells into corneal epithelial cells.

Non-patent document 4 describes that lens precursor cells were induced by adhesion culture of human ES cells in the presence of BMP4, BMP7, and FGF2. Non-patent document 5 describes that the corneal epithelium was induced by adhesion culture of mouse iPS cells on a PA6 feeder layer. Non-patent document 6 describes that corneal stromal cells were induced by adhesion culture of human ES cells in the presence of feeder cells. Non-patent document 7 describes that human ES cells were induced into cornea-like cells by adhesion culture. However, none of these documents disclose that pluripotent stem cells were cultured in suspension to sterically form an anterior eye segment tissue such as cornea, lens and the like.

DOCUMENT LIST

Patent Documents patent document 1: WO 2009/148170
patent document 2: WO 2011/055855

Non-Patent Documents non-patent document 1: Nakano et al., Cell Stem Cell, 10(6): 771-785, 2012
non-patent document 2: Eiraku et al., Nature, 472(7341): 51-56, 2011
non-patent document 3: Hayashi et al., PLOS ONE, 7(9): e45435, 2012
non-patent document 4: Yang et al., FASEB J., 24: 3274-3283, 2010
non-patent document 5: Yoshida et al., PLOS ONE, 6(12): e28856, 2011
non-patent document 6: Chan et al., PLOS ONE, 8(2): e56831, 2013
non-patent document 7: Ahmad et al., Stem Cells, 25: 1145-1155, 2007

SUMMARY OF THE INVENTION

Problems to be Solved by the Invention

An object of the present invention is to develop a highly practical method for inducing selective differentiation of pluripotent stem cells into an anterior eye segment tissue or a precursor tissue thereof.

Means of Solving the Problems

The present inventors have conducted intensive studies and found that self-organization of anterior eye segment tissues (lens and cornea) can be induced and steric formation of the cornea and lens can be efficiently performed by treating aggregates of human pluripotent stem cells with BMP4 under suspension culture. By applying a BMP4 treatment in the initial process of the method of inducing self-organization of steric retina (SFEBq method), which was developed by the present inventors, they have succeeded in forming a surface ectoderm in a self-organizing manner in the surface of a retinal epithelial tissue aggregate formed in aggregates, and spontaneously causing "differentiation induction of the surface ectoderm into anterior eye segment precursor tissues (lens placode and corneal placode) by retina" which is seen in the embryo of the living body. As a result, a suspended aggregate that self-organized retina in the inside, and thickened lens and corneal epithelial precursor tissue in the surface could be sterically formed.

They have further succeeded in spontaneous invagination of the lens placode inside the aggregate, and formation of the lens vesicle by continuously culturing the suspended aggregate.

The cornea of an adult consists of three layers of epithelium, stroma and endothelium from the surface to the inside. They have further succeeded in allowing aggregates to express a plurality of marker proteins observed in the corneal epithelium of an adult by culturing the above-mentioned aggregates for a long term. While the stroma and endothelium are known to be developed from mesenchymal cells derived from neural crest cells, rather than from surface ectoderm, when the above-mentioned aggregate was cultured for a long term, mesenchymal cells could also be developed in the aggregate in addition to the retinal tissue and corneal epithelial tissue, as a result of which, they have found that steric cornea having both a corneal epithelium layer and a mesenchymal cell layer (corresponding to stroma and endothelium) in combination can be formed.

The present inventors have conducted further studies based on the above-mentioned findings and completed the present invention.

Accordingly, the present invention is as follows:
[1] A production method of a cell aggregate comprising an anterior eye segment tissue or a partial structure thereof, or a precursor tissue thereof, comprising culturing an aggregate of pluripotent stem cells in suspension in the presence of a bone morphogenic factor signal transduction pathway activating substance.

[2] The method of [1], wherein the aggregate of pluripotent stem cells is cultured in suspension in the absence of a bone morphogenic factor signal transduction pathway activating substance, prior to the suspension culture in the presence of a bone morphogenic factor signal transduction pathway activating substance.

[3] The method of [1] or [2], wherein the bone morphogenic factor signal transduction pathway activating substance is BMP4.

[4] The method of [3], wherein BMP4 has a concentration of 1-5 nM.

[5] The production method of any of [1]-[4], wherein the suspension culture is performed entirely or partially in the presence of a fibroblast growth factor.

[6] The method of any of [1]-[5], wherein the pluripotent stem cells are embryonic stem cells or induced pluripotent stem cells.

[7] The method of any of [1]-[6], wherein the pluripotent stem cells are derived from human.

[8] The method of any of [1]-[7], wherein the suspension culture is performed in the absence of a feeder cell.

[9] The method of any of [1]-[8], wherein the cell aggregate further comprises a neural retinal tissue.

[10] The method of any of [1]-[9], wherein the anterior eye segment tissue is cornea and/or lens.

[11] The method of any of [1]-[10], wherein the cell aggregate comprises corneal epithelium as a partial structure of the anterior eye segment tissue, and further comprises a mesenchymal tissue, or corneal stroma and/or corneal endothelium derived therefrom.

[12] The method of [11], wherein the corneal epithelium is stratified.

[13] The method of any of [1]-[12], further comprising separating the anterior eye segment tissue or partial structure thereof or precursor tissue thereof from the cell aggregate.

[14] The method of [13], wherein the anterior eye segment tissue or partial structure thereof, or precursor tissue thereof is separated together with a neural retinal tissue.

[15] A cell aggregate obtained by the method of any of [1]-[12].

[16] An anterior eye segment tissue or a partial structure thereof, or a precursor tissue thereof, which is obtained by the method of [13] or [14].

Effect of the Invention

According to the present invention, anterior eye segment tissues such as lens, cornea and the like or a partial structure thereof, or a precursor tissue thereof can be sterically formed under suspension culture capable of affording a high-throughput.

According to the present invention, anterior eye segment tissues such as lens, cornea and the like or a partial structure thereof, or a precursor tissue thereof can be induced from pluripotent stem cells with high efficiency unattainable by conventional methods. In one embodiment wherein aggregates are formed in culture compartments having a comparatively small volume such as a 96 well plate, aggregates containing corneal precursor tissues at an efficiency of not less than 80% can be formed, and cell aggregates containing lens precursor tissues at an efficiency of not less than 20% can be obtained.

According to the present invention, anterior eye segment tissues such as lens, cornea and the like or a partial structure thereof, or a precursor tissue thereof can be induced from pluripotent stem cells in "a short period" unattainable by conventional methods. In one embodiment according to the present invention, lens and corneal epithelium can be induced from pluripotent stem cells in about 3 weeks from the start of the differentiation culture, which conventionally required at least twice as long.

According to the present invention, retina, lens and cornea, which are co-present in eyes of living body, can be sterically formed adjoiningly from pluripotent stem cells. Therefore, a culture environment for inartificial tissue development similar to that in the body can be reproduced.

According to the present invention, corneal epithelium and neural crest-derived mesenchymal tissues adjacent thereto, which form corneal endothelium and corneal stroma, can be simultaneously formed in aggregates to produce corneal precursor tissues having precursor tissues of epithelium, stroma and endothelium in a lamellar state.

According to the present invention, corneal epithelium having a stratified epithelial structure characteristic of mature cornea, comprising squamous epithelium as a surface layer and cuboidal epithelium as a deep layer, can be formed.

According to the present invention, corneal precursor tissues can be selectively formed on the surface layer of aggregates, and corneal progenitor cells can be separated at high purity even without using FACS and the like.

DESCRIPTION OF EMBODIMENTS

Figure 1A:
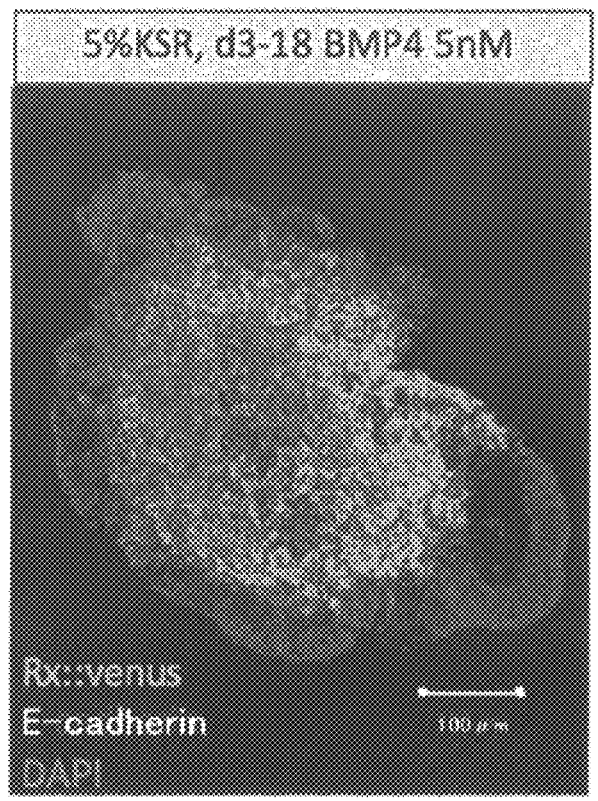
FIG. 1A shows that a Rx::venus negative, E-cadherin positive epithelial cell layer different from neural retina is formed in the surface layer of human ES cell aggregate (day 14) obtained by the SFEBq method under BMP4 addition conditions.

The present invention provides a production method of a cell aggregate containing an anterior eye segment tissue or a partial structure thereof, or a precursor tissue thereof, and a neural retinal tissue, which comprises culturing an aggregate of pluripotent stem cells in suspension in the presence of a bone morphogenic factor signal transduction pathway activating substance.

The present invention is explained in detail in the following.

(1) Pluripotent Stem Cell

The "pluripotent stem cell" refers to a cell having both the potential for differentiating into all cells constituting the body (differentiation pluripotency), and the potential for producing daughter cells having the same differentiation potency via cell division (self-replication competence).

The differentiation pluripotency can be evaluated by transplanting the cells of an evaluation target into a nude mouse, and testing the presence or absence of formation of teratoma containing each cell of three germ layers (ectoderm, mesoderm, endoderm).

Examples of the pluripotent stem cell include embryonic stem cell (ES cell), embryonic germ cell (EG cell), induced pluripotent stem cell (iPS cell) and the like, and the pluripotent stem cell is not limited as long as it has both the differentiation pluripotency and the self-replication competence. In the present invention, embryonic stem cells or induced pluripotent stem cells are preferably used.

Embryonic stem cells (ES cell) can be established by culturing, for example, a pre-implantation early embryo, an inner cell mass that constitutes the early embryo, a single blastomere and the like (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (1998)), Akira IRITANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature 35 Genetics, 24, 109 (2000), Tachibana et al. (Human Embryonic Stem Cells Derived by Somatic Cell Nuclear Transfer, Cell (2013) in press)). As an early embryo, a parthenogenetic embryo may also be used (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)).

Fusion ES cell obtained by cell fusion of ES cell and somatic cell is also included in the embryonic stem cells used for the method of the present invention.

Embryonic stem cells are available from appropriate organizations, and commercial products may be purchased. For example, the human embryonic stem cells KhES-1, KhES-2 and KhES-3 are available from the Institute for Frontier Medical Sciences, Kyoto University.

Embryonic germ cells (EG cell) can be established by culturing primordial germ cells in the presence of LIF, bFGF, SCF and the like (Matsui et al., Cell, 70, 841-847 (1992), Shamblott et al., Proc. Natl. Acad. Sci. USA, 95(23), 13726-13731 (1998), Turnpenny et al., Stem Cells, 21(5), 598-609, (2003)).

Induced pluripotent stem cell (iPS cell) refers to a cell that artificially acquired differentiation pluripotency and self-replication competence by contacting a somatic cell (e.g., fibroblast, skin cell, lymphocyte etc.) with a nuclear reprogramming factor. iPS cell was found for the first time by a method including introduction of nuclear reprogramming factors composed of Oct3/4, Sox2, Klf4 and c-Myc into somatic cells (e.g., fibroblast, skin cell etc.) (Cell, 126: p. 663-676, 2006). Thereafter, many researchers have made various improvements in the combination of reprogramming factors and introduction method of the factors, and various production methods of induced pluripotent stem cell have been reported.

The nuclear reprogramming factors may be configured with any substance, such as a proteinous factor or a nucleic acid that encodes the same (including forms incorporated in a vector), or a low molecular compound, as long as it is a substance (substances) capable of inducing a cell having differentiation pluripotency and self-replication competence from a somatic cell such as fibroblast and the like. When the nuclear reprogramming factor is a proteinous factor or a nucleic acid that encodes the same, preferable nuclear reprogramming factors are exemplified by the following combinations (hereinafter, only the names for proteinous factors are shown).

(1) Oct3/4, Klf4, Sox2, c-Myc (wherein Sox2 is replaceable with Sox1, Sox3, Sox15, Sox17 or Sox18. Klf4 is replaceable with Klf1, Klf2 or Klf5. Furthermore, c-Myc is replaceable with T58A (active form mutant), N-Myc or L-Myc.)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF Among these combinations, when use of the obtained iPS cell for therapeutic application is considered, a combination of the three factors of Oct3/4, Sox2 and Klf4 is preferable. On the other hand, when use of the iPS cell for therapeutic application is not considered (e.g., used as an investigational tool for drug discovery screening and the like), four factors consisting of Oct3/4, Klf4, Sox2 and c-Myc, or 5 factors by adding Lin28 or Nanog thereto are preferable.

iPS cell is preferably used for autologous transplantation.

A pluripotent stem cell obtained by modifying genes in a chromosome by a known genetic engineering method can also be used in the present invention. The pluripotent stem cell may be a cell wherein a labeling gene (e.g., fluorescent protein such as GFP etc.) has been knocked in a gene encoding a differentiation marker in an in-frame manner by a known method, which cell can be identified to have reached the corresponding differentiation stage by using the expression of the labeling gene as an index.

As the pluripotent stem cell, warm-blooded animal pluripotent stem cells, preferably mammalian pluripotent stem cells, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees. Pluripotent stem cell is preferably pluripotent stem cell of rodents (mouse, rat etc.) or primates (human etc.) and most preferably human pluripotent stem cell.

Pluripotent stem cells can be cultured for maintenance by a method known per se. For example, from the aspects of clinical application, pluripotent stem cells are preferably maintained by serum-free culture using serum alternatives such as Knockout™ Serum Replacement (KSR) and the like, or feeder-free cell culture.

The pluripotent stem cells to be used in the present invention are preferably isolated. Being "isolated" means that an operation to remove factors other than the target cell or component has been performed, and the cell or component is no longer in a natural state. The purity of the "isolated human pluripotent stem cells" (percentage of the number of human pluripotent stem cells to the total cell number) is generally not less than 70%, preferably not less than 80%, more preferably not less than 90%, further preferably not less than 99%, most preferably 100%.

(2) Tissues which can be Induced by Differentiation by the Method of the Present Invention According to the production method of the present invention, a cell aggregate containing an anterior eye segment tissue or a partial structure thereof, or a precursor tissue thereof can be obtained by inducing, in a pluripotent stem cell aggregate, differentiation of pluripotent cells into an anterior eye segment tissue or a partial structure thereof, or a precursor tissue thereof.

The anterior eye segment refers to a part anterior to the ora serrata of the eyeball. The anterior eye segment tissue refers to a tissue constituting the anterior eye segment, and includes tissues such as cornea, lens, iris, ciliary body, anterior and posterior chambers, zonule, anterior vitreous body and anterior sclera, as well as conjunctiva and eyelid and the like in the external eye segment and a partial structure thereof. The anterior eye segment tissue or a partial structure thereof, or a precursor tissue thereof contained in a cell aggregate produced by the method of the present invention preferably includes i) cornea, a partial structure thereof, or a precursor tissue thereof, and/or ii) crystalline lens, a partial structure thereof, or a precursor tissue thereof.

Cornea is a transparent watch glass-like tissue occupying about ⅙ of a part anterior to the outer layer of the eye wall. Examples of the partial structure of cornea include, but are not limited to, corneal epithelium, Bowman's membrane, corneal stroma, Descemet's membrane, corneal endothelium and the like. Cornea is generally composed of 5 layers consisting of corneal epithelium, Bowman's membrane, corneal stroma, Descemet's membrane, and corneal endothelium, in this order from the body surface side. Induction of cornea, a partial structure thereof, or a precursor tissue thereof can be confirmed by the expression of a marker. Examples of the marker of cornea, a partial structure thereof, or a precursor tissue thereof include pan-cytokeratin (corneal epithelial precursor tissue), E-cadherin (corneal epithelial precursor tissue), cytokeratin 3 (corneal epithelium), cytokeratin 12 (corneal epithelium), cytokeratin 14 (corneal epithelium), p63 (corneal epithelium), ZO-1 (corneal epithelium), PDGFR-α (corneal stroma, corneal endothelium, or a precursor tissue thereof), Pitx2 (precursor tissue of corneal stroma and corneal endothelium), ABCG2 (precursor tissue of corneal stroma and corneal endothelium) and the like. In one embodiment, a precursor tissue of corneal epithelium contained in a cell aggregate produced by the method of the present invention is a pancytokeratin positive and E-cadherin positive epithelial cell layer. In one embodiment, the corneal epithelium contained in a cell aggregate produced by the method of the present invention is a cytokeratin 3 positive, cytokeratin 12 positive, cytokeratin 14 positive, p63 positive and ZO-1 positive epithelial structure. In one embodiment, a precursor tissue of corneal stroma and corneal endothelium contained in a cell aggregate produced by the method of the present invention is an aggregate layer of mesenchymal cells. In one embodiment, the aggregate layer of mesenchymal cells is PDGFR-α positive, or Pitx2 positive and ABCG2 positive. While corneal stroma and corneal endothelium are both derived from mesenchymal cells, corneal endothelium shows an epithelized endothelial cell layer-like form. Morphological observation in addition to the above-mentioned analysis of marker expression enables distinction of corneal stroma (or a precursor tissue thereof) from corneal endothelium (or a precursor tissue thereof), and confirmation of the induction of corneal endothelium or a precursor tissue thereof.

Lens is a tissue that plays a role of a lens that refracts the light that enters the eyeball from the outside and focuses on the retina. Examples of the partial structure of lens include, but are not limited to, lens epithelium, lens nucleus, lens capsule, and the like. Examples of the precursor tissue of lens include lens placode, lens vesicle and the like. Lens placode is a lens precursor tissue composed of a thickened surface ectoderm cell layer. In embryogenic development, it is formed by the contact of eye cup with surface ectoderm, which thickens the contact region. A lens vesicle is a vesicle formed by invagination of lens placode. Induction of a lens, a partial structure thereof, or a precursor tissue thereof can be confirmed by the expression of a marker. Examples of the marker of a lens, a partial structure thereof, or a precursor tissue thereof include, but are not limited to, L-Maf (lens precursor tissue), α, β and γ crystallines (lens) and the like. In one embodiment, lens placode is an L-Maf positive thickened surface ectoderm cell layer. In one embodiment, the lens vesicle is an L-Maf positive vesicle.

Neural retina refers to a part in retina that senses the light, and contains at least one kind of retinal cell. As the retinal cell, any cell constituting the retina can be mentioned and is not particularly limited. Examples thereof include photoreceptor, horizontal cell, bipolar cell, amacrine cell, retinal ganglion cell and the like. Induction of retinal cell can be confirmed by the expression of a cell marker. Examples of the retinal cell marker include, but are not limited to, Rx (retinal progenitor cell), PAX6 (progenitor cell), Crx (progenitor cell of photoreceptor), Chx10 (bipolar cell), L7 (bipolar cell), Tuj1 (ganglion cell), Brn3 (ganglion cell), Calretinin (amacrine cell), Calbindin (horizontal cell), Rhodopsin (photoreceptor), recoverin (photoreceptor), RPE65 (pigment epithelial cell), Mitf (pigment epithelial cell) and the like. In one embodiment, neural retinal tissue contained in a cell aggregate produced by the method of the present invention is an Rx positive, Chx10 positive epidermal tissue.

(3) Formation of Pluripotent Stem Cell Aggregate

A pluripotent stem cell aggregate can be obtained by culturing dispersed pluripotent stem cells under conditions that are non-adhesive to the culture vessel (i.e., culturing in suspension), and assembling plural pluripotent stem cells to allow for aggregate formation.

A culture vessel used for the aggregate formation is not particularly limited, and examples thereof include flasks, tissue culture flasks, dishes, Petri dishes, tissue culture dishes, multi-dishes, microplates, micro-well plates, micropores, multi-plates, multi-well plates, chamber slides, Petri dishes, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be cell non-adherent, culture vessels whose surfaces have not undergone an artificial treatment for improving the cell adhesiveness (e.g., coating treatment with an extracellular matrix and the like), and the like.

The medium to be used for aggregate formation can be prepared using a medium used for culturing animal cells as a basal medium. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, a mixed medium thereof and the like.

To avoid an adverse influence on the differentiation induction of a pluripotent stem cell into an anterior eye segment tissue or a partial structure thereof, or a precursor tissue thereof, the medium used for aggregate formation is preferably a serum-free medium. The serum-free medium means a medium free of an unadjusted or unpurified serum. A medium containing purified components derived from blood and components derived from animal tissue (e.g., cytokine) corresponds to a serum-free medium.

The medium used for aggregate formation may contain a serum alternative. The serum alternative can, for example, be one comprising as appropriate an albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of the method of the present invention, commercially available serum alternatives can be utilized. Examples of such commercially available serum alternatives include Knockout Serum Replacement (KSR, produced by Invitrogen), Chemically-defined Lipid Concentrated (produced by Gibco Company) and Glutamax (produced by Gibco Company).

A medium to be used for aggregate formation can contain other additive as long as induction of differentiation of pluripotent stem cells into an anterior eye segment tissue or a partial structure thereof, or a precursor tissue thereof is not adversely influenced. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

A medium to be used for aggregate formation may be a below-mentioned medium used for induction of differentiation of pluripotent stem cells into an anterior eye segment tissue or a partial structure thereof, or a precursor tissue thereof.

For formation of a pluripotent stem cell aggregate, pluripotent stem cells are collected from passage culture and dispersed to a single cell state or near single cell state. Pluripotent stem cells are dispersed with an appropriate cell dissociation solution. Examples of the cell dissociation solution include EDTA; protease such as trypsin, collagenase IV, metalloproteinase and the like, and the like, which are used alone or in an appropriate combination. Of these, one showing low cell toxicity is preferable, and examples of such cell dissociation solution include commercially available products such as DISPASE (EIDIA), TrypLE (Invitrogen), Accutase (MILLIPORE) and the like. Of these, Accutase is preferably used since it does not easily cause cell death of pluripotent stem cells (particularly human pluripotent stem cells) even when the cells are dissociated to a near single cell state. The dispersed pluripotent stem cells are suspended in the above-mentioned medium.

To suppress cell death of pluripotent stem cells (particularly, human pluripotent stem cells) induced by dispersion, it is preferable to add an inhibitor of Rho-associated coiled-coil kinase (ROCK) from the start of cultivation (JP-A-2008-99662). Examples of the ROCK inhibitor include Y-27632 ((+)-(R)-trans-4-(1-aminoethyl)-N-(4-pyridyl)cyclohexanecarboxamide dihydrochloride) and the like. The concentration of the ROCK inhibitor used for suspension culture is a concentration capable of suppressing cell death of pluripotent stem cells induced by dispersion. For example, for Y-27632, this concentration is normally about 0.1 to 200 µM, preferably about 2 to 50 µM.

A suspension of the dispersed pluripotent stem cells is seeded in the above-mentioned culture vessel and the dispersed pluripotent stem cells are cultured under conditions that are non-adhesive to the cell culture vessel, whereby the plural pluripotent stem cells are assembled to form an aggregate. In this case, dispersed pluripotent stem cells may be seeded in a comparatively large culture vessel such as a 10-cm dish to simultaneously form plural pluripotent stem cell aggregates in one culture compartment. However, the size of aggregates, and the number of pluripotent stem cells contained therein may vary widely, and such variation may cause difference in the levels of differentiation of pluripotent stem cells into an anterior eye segment tissue or a partial structure thereof, or a precursor tissue thereof between aggregates, which in turn may lower the efficiency of differentiation induction. Therefore, it is preferable to rapidly coagulate the dispersed pluripotent stem cells to form one aggregate in one culture compartment. Examples of the method for rapidly coagulating the dispersed pluripotent stem cells include the following methods:

(1) A method including enclosing dispersed pluripotent stem cells in a culture compartment having a comparatively small volume (e.g., not more than 1 ml, not more than 500 µl, not more than 200 µl, not more than 100 µl) to form one aggregate in the compartment. Preferably, the culture compartment is stood still after enclosing the dispersed pluripotent stem cells. Examples of the culture compartment include, but are not limited to, a well in a multi-well plate (384-well, 192-well, 96-well, 48-well, 24-well etc.), micropore, chamber slide and the like, tube, a droplet of a medium in hanging drop method and the like. The dispersed pluripotent stem cells enclosed in the compartment are precipitated on one spot due to the gravity, or the cells adhere to each other to form one aggregate in one culture compartment. The shape of the bottom of the multiwall plate, micropore, chamber slide, tube and the like is preferably U-bottom or V-bottom to facilitate precipitation of the dispersed pluripotent stem cells on one spot.

(2) A method including placing dispersed pluripotent stem cells in a centrifugation tube, centrifuging same to allow for precipitation of pluripotent stem cells on one spot, thereby forming one aggregate in the tube.

The number of pluripotent stem cells to be seeded in one culture compartment is not particularly limited as long as one aggregate is formed per one culture compartment, and differentiation of pluripotent stem cells into an anterior eye segment tissue or a partial structure thereof, or a precursor tissue thereof can be induced in the aggregate by the method of the present invention. Generally, about $1 \times 10^3$-about $5 \times 10^4$, preferably about $1 \times 10^3$-about $2 \times 10^4$, more preferably about $2 \times 10^3$-about $1.2 \times 10^4$ of pluripotent stem cells are seeded in one culture compartment. Then, by rapidly coagulating the pluripotent stem cells, one cell aggregate generally composed of about $1 \times 10^3$-about $5 \times 10^4$, preferably about $1 \times 10^3$-about $2 \times 10^4$, more preferably about $2 \times 10^3$-about $1.2 \times 10^4$ pluripotent stem cells is formed per one culture compartment.

The time up to aggregate formation can be determined as appropriate as long as one aggregate is formed per one compartment, and differentiation of pluripotent stem cells into an anterior eye segment tissue or a partial structure thereof, or a precursor tissue thereof can be induced in the aggregate by the method of the present invention. By shortening the time, efficient induction of differentiation into the object anterior eye segment tissue or a partial structure thereof, or a precursor tissue thereof is expected, and therefore, said time is preferably shorter. Preferably, pluripotent stem cell aggregate is formed within 24 hr, more preferably within 12 hr, further preferably within 6 hr, most preferably in 2-3 hr. The time up to the aggregate formation can be adjusted as appropriate by choosing a tool for cell aggregation, centrifugal conditions and the like by those skilled in the art.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Furthermore, plural culture compartments under the same culture conditions are prepared and one pluripotent stem cell aggregate is formed in each culture compartment, whereby a qualitatively uniform population of pluripotent stem cell aggregates can be obtained. Whether pluripotent stem cell aggregates are qualitatively uniform can be evaluated on the basis of the size of the aggregate mass and the number of cells therein, macroscopic morphology, microscopic morphology and homogeneity thereof as analyzed by histological staining, the expression of differentiation and un-differentiation markers and homogeneity thereof, the regulation of the expression of differentiation markers and synchronicity thereof, reproducibility of differentiation efficiency among aggregates, and the like. In one embodiment, a population of the pluripotent stem cell aggregates to be used in the method of the present invention contains a uniform number of pluripotent stem cells in the aggregates. A population of pluripotent stem cell aggregates being "uniform" in a particular parameter means that not less than 90% of the total aggregates in a population thereof falls within the range of mean of the parameter in the aggregate population ±10%, preferably ±5%.

(4) Induction of Anterior Eye Segment Tissue or Partial Structure Thereof, or Precursor Tissue Thereof The production method of the present invention comprises culturing pluripotent stem cell aggregate in suspension in the presence of a bone morphogenic factor signal transduction pathway activating substance such as BMP4. By culturing pluripotent stem cell aggregate in suspension in a medium containing a bone morphogenic factor signal transduction pathway activating substance, differentiation into an anterior eye segment tissue or a partial structure thereof, or a precursor tissue thereof from the pluripotent stem cells is induced, and a cell aggregate containing an anterior eye segment tissue or a partial structure thereof, or a precursor tissue thereof is produced.

According to the present invention, self-organization of an anterior eye segment tissue is induced by treating a pluripotent stem cell aggregate with a bone morphogenic factor signal transduction pathway activating substance such as BMP4 under suspension culture conditions, whereby an anterior eye segment tissue such as cornea, lens and the like, a partial structure thereof, or a precursor tissue thereof can be sterically formed. According to one embodiment of the present invention, self-organization of neural retina is induced by culturing a pluripotent stem cell aggregate in suspension. By a treatment with a bone morphogenic factor signal transduction pathway activating substance during this process, surface ectoderm is formed in a self-organization manner in the surface of a retinal epithelial tissue aggregate formed in the aggregate, and "induction, by retina, of differentiation of a precursor tissue (lens placode, corneal placode etc.) of an anterior eye segment tissue from the surface ectoderm", which is observed in the process of embryogenic development in vivo, can be spontaneously caused to take place in vitro. As a result, neural retina is self-organized inside the cell aggregate, and an anterior eye segment tissue, a partial structure thereof, or a precursor tissue thereof (e.g., lens placode, corneal epithelial precursor tissue) is self-organized in the surface thereof. That is, in one embodiment, the cell aggregate obtained by the present invention further contains a neural retinal tissue. In this way, a cell aggregate comprising an anterior eye segment tissue or a partial structure thereof, or a precursor tissue thereof constituting the surface layer of the cell aggregate, and a neural retinal tissue in the inside of the cell aggregate, wherein the anterior eye segment tissue or a partial structure thereof, or a precursor tissue thereof is adjacent to the neural retinal tissue, is obtained.

"culturing in suspension" a pluripotent stem cell aggregate refers to culturing an aggregate of pluripotent stem cells in a medium under conditions that are non-adhesive to the culture vessel. This enables steric formation which is difficult to achieve in conventional adhesion culture.

The medium used for suspension culture contains a bone morphogenic factor signal transduction pathway activating substance. The bone morphogenic factor signal transduction pathway activating substance is any substance that activates the pathway through which signals are transmitted upon binding of a bone morphogenic factor and a receptor. Examples of the bone morphogenic factor signal transduction pathway activating substance include BMP2, BMP4, BMP7, GDF5 and the like. Preferably, the bone morphogenic factor signal transduction pathway activating substance is BMP4. While BMP4 is mainly described below, the bone morphogenic factor signal transduction pathway activating substance to be used in the present invention is not limited to BMP4. BMP4 is a known cytokine, and the amino acid sequence thereof is also known. BMP4 to be used in the present invention is mammalian BMP4. Examples of the mammal include experiment animals such as rodents such as mouse, rat, hamster, guinea pig and the like, and the like; domestic animals such as swine, bovine, goat, horse, sheep and the like; companion animals such as dog, cat and the like; and primates such as human, monkey, orangutan, chimpanzee and the like. BMP4 is preferably BMP4 of rodents (mouse, rat etc.) or primates (human etc.), most preferably human BMP4. Human BMP4 means that BMP4 has the amino acid sequence of BMP4 naturally expressed in the human body. Examples of the representative amino acid sequence of human BMP4 include NCBI accession numbers NP_001193.2 (updated on Jun. 15, 2013), NP_570911.2 (updated on Jun. 15, 2013), NP_570912.2 (updated on Jun. 15, 2013), amino acid sequence (mature form human BMP4 amino acid sequence) obtained by removing the N-terminal signal sequence (1-24) from each of these amino acid sequences and the like.

The concentration of the bone morphogenic factor signal transduction pathway activating substance in the medium can be appropriately determined within a range in which differentiation of pluripotent stem cells into an anterior eye segment tissue or a partial structure thereof, or a precursor tissue thereof can be induced in the aggregate. When BMP4 is used as a bone morphogenic factor signal transduction pathway activating substance, the concentration thereof is generally 0.1-50 nM, preferably 1-5 nM. The BMP4 concentration may be maintained constant during the culture period or varied. For example, the BMP4 concentration can be first set to 3-7 nM, preferably 4-6 nM, more preferably about 5 nM, and then set to 0-3 nM, preferably 0.5-2 nM, more preferably about 1 nM.

Culture in a medium containing a bone morphogenic factor signal transduction pathway activating substance (BMP4 etc.) does not need to be performed throughout the period up to the induction of an anterior eye segment tissue or a partial structure thereof, or a precursor thereof from pluripotent stem cells, and only need to be performed in a part of the period. For example, a pluripotent stem cell aggregate is cultured in suspension in the absence of a bone morphogenic factor signal transduction pathway activating substance (BMP4 etc.) before suspension culture thereof in the presence of a bone morphogenic factor signal transduction pathway activating substance (BMP4 etc.). In one embodiment, a pluripotent stem cell aggregate is cultured in suspension in the absence of a bone morphogenic factor signal transduction pathway activating substance (BMP4 etc.) for 1-5 days, preferably 1-3 days, after formation of the pluripotent stem cell aggregate, and thereafter, the suspension culture may be continued after changing the medium to one containing a bone morphogenic factor signal transduction pathway activating substance (BMP4 etc.).

The medium to be used for suspension culture of aggregate can be prepared using a medium used for culturing animal cells as a basal medium. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, a mixed medium thereof and the like.

To avoid an adverse influence on the induction of differentiation of pluripotent stem cells into an anterior eye segment tissue or a partial structure thereof, or a precursor tissue thereof, the medium used for culturing aggregates in suspension is preferably a serum-free medium.

The medium used for suspension culture of aggregates may contain a serum alternative. The serum alternative can, for example, be one comprising as appropriate an albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of a method of the present invention, commercially available serum alternatives can be utilized. Examples of such commercially available serum alternatives include Knockout Serum Replacement (KSR) (produced by Invitrogen), Chemically-defined Lipid Concentrated (produced by Gibco Company) and Glutamax (produced by Gibco Company).

The medium used for culturing the aggregate in suspension can contain other additive as long as an adverse influence is not exerted on the induction of differentiation of pluripotent stem cells into an anterior eye segment tissue or a partial structure thereof, or a precursor tissue thereof. Examples of the additive include, but are not limited to, insulin, iron source (e.g., transferrin etc.), mineral (e.g., sodium selenate etc.), saccharides (e.g., glucose etc.), organic acid (e.g., pyruvic acid, lactic acid etc.), serum protein (e.g., albumin etc.), amino acid (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation of pluripotent stem cells into an anterior eye segment tissue or a partial structure thereof, or a precursor tissue thereof, the medium used for floating-culturing aggregates is preferably a growth-factor-free chemically defined medium (gfCDM) added with a serum alternative (KSR etc.). The "growth factor" here encompasses pattern formation factors (excluding bone morphogenic factor signal transduction pathway activating substances) such as Fgf, Wnt, Nodal, Notch, Shh and the like; insulin and lipid-rich albumin. Examples of the growth-factor-free chemically defined medium include gfCDM disclosed in Wataya et al, Proc Natl Acad Sci USA, 105(33): 11796-11801, 2008. gfCDM is a 1:1 mixed medium of IMDM and Ham's F-12 which contains 1× chemically defined lipid concentrate, monothioglycerol (450 µM), purified BSA and human apo-transferrin (150 µg/ml final).

A culture vessel to be used for suspension-culture of aggregates is not particularly limited. Such culture vessel includes, for example, flasks, tissue culture flasks, dishes, Petri dishes, tissue culture dishes, multi-dishes, microplates, micro-well plates, micropores, multi-plates, multi-well plates, chamber slides, Petri dishes, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be non-cell-adherent, culture vessels whose surfaces have not undergone an artificial treatment for improving the cell adhesiveness (e.g., coating treatment with an extracellular matrix and the like), and the like.

Suspension culture of the aggregate may be performed in the presence or absence of feeder cells as long as the differentiation induction from pluripotent stem cells into an anterior eye segment tissue or a partial structure thereof, or a precursor tissue thereof is possible. To avoid contamination with undefined factors, the suspension culture of aggregate is preferably performed in the absence of feeder cells.

Other culturing conditions for suspension culture of the aggregate, such as culturing temperature, $CO_2$ concentration and $O_2$ concentration, can be set as appropriate. The culturing temperature is not particularly limited, and is, for example, about 30 to 40° C., preferably about 37° C. The $CO_2$ concentration is, for example, about 1 to 10%, preferably about 5%. The $O_2$ concentration is, for example, about 20-40%.

In a preferable embodiment, a qualitatively uniform population of pluripotent stem cell aggregates is cultured in suspension in a medium containing a bone morphogenic factor signal transduction pathway activating substance (BMP4 etc.). Using a qualitatively uniform population of pluripotent stem cell aggregates, difference in levels of differentiation into an anterior eye segment tissue or a partial structure thereof, or a precursor tissue thereof between aggregates can be suppressed to the minimum, and the efficiency of the object differentiation induction can be improved. Suspension culture of a qualitatively uniform population of pluripotent stem cell aggregates encompasses the following embodiments.

(1) Plural culture compartments are prepared, and a qualitatively uniform population of pluripotent stem cell aggregates is seeded such that one pluripotent stem cell aggregate is contained in one culture compartment (e.g., one pluripotent stem cell aggregate is placed in each well of 96 well plate). In each culture compartment, one pluripotent stem cell aggregate is cultured in suspension in a medium containing a bone morphogenic factor signal transduction pathway activating substance (BMP4 etc.).

(2) A qualitatively uniform population of pluripotent stem cell aggregates is seeded such that plural pluripotent stem cell aggregates are contained in one culture compartment (e.g., plural pluripotent stem cell aggregates are placed in a 10 cm dish). In the culture compartment, plural pluripotent stem cell aggregates are cultured in suspension in a medium containing a bone morphogenic factor signal transduction pathway activating substance (BMP4 etc.).

Any of the embodiments (1) and (2) may be employed for the method of the present invention and the embodiment may be changed during culture (from embodiment (1) to embodiment (2), or from embodiment (2) to embodiment (1)). To avoid interaction between aggregates and to achieve stable differentiation induction, embodiment (1) is preferable.

As mentioned above, since self-organization of the anterior eye segment tissue is induced in a cell aggregate in the method of the present invention, the differentiation stage of an anterior eye segment tissue or a partial structure thereof, or a precursor tissue thereof contained in the cell aggregate proceeds with the progress of time. Therefore, the culture period and culture conditions are preferably adjusted as appropriate according to the object anterior eye segment tissue or a partial structure thereof, or a precursor tissue thereof. In the following (5)-(11), one embodiment of the present invention is explained along the time series, which is an exemplification of the present invention and does not limit the present invention.

(5) Induction of Neural Retinal Tissue

When a pluripotent stem cell aggregate is cultured in suspension in a medium containing a bone morphogenic factor signal transduction pathway activating substance (BMP4 etc.), a neural retinal tissue is induced in the inside of the aggregate. Induction of the neural retinal tissue can be confirmed using expression of a neural retinal tissue marker (e.g., Rx, Chx10) or formation of a neuroepithelium-like structure (pseudostratified columnar epithelium) as an index. The period necessary for the induction of the neural retinal tissue varies depending on the culture conditions, and the kind of a mammal from which the pluripotent stem cells are derived, and cannot be generally specified. However, when human pluripotent stem cells are used, a neural retinal tissue is induced in the inside of the aggregate in, for example, 8, 9, 10, 11, 12, 13, 14 or 15 days from the start of the suspension culture of the pluripotent stem cell aggregate.

(6) Induction of Corneal Epithelial Precursor Tissue and/or a Lens Placode

When the aggregate containing a neural retinal tissue in the inside, which is obtained in the above-mentioned (5), is continuously cultured in suspension in a medium containing a bone morphogenic factor signal transduction pathway activating substance (BMP4 etc.), an ectodermal epithelial cell layer is formed on the outside of the neural retinal tissue, and the neural retinal tissue induces differentiation of the ectodermal epithelial cell layer into a corneal epithelial precursor tissue and/or a lens placode to form a corneal epithelial precursor tissue and/or a lens placode in the surface layer of the cell aggregate. In the aggregate, the corneal epithelial precursor tissue and/or the lens placode constitute(s) the surface layer of the cell aggregate, the neural retinal tissue is contained in the inside of the cell aggregate, and the corneal epithelial precursor tissue and/or the lens placode are(is) adjacent to the neural retinal tissue. Induction of the corneal epithelial precursor tissue and/or the lens placode can be confirmed using expression of a corneal epithelial precursor tissue marker (e.g., pancytokeratin, E-cadherin) and a lens placode marker (e.g., L-Maf), or formation of a thickened epithelial cell layer as an index. The period necessary for the induction of the corneal epithelial precursor tissue and/or the lens placode varies depending on the culture conditions, and the kind of a mammal from which the pluripotent stem cells are derived, and cannot be specified generally. However, when human pluripotent stem cells are used, a corneal epithelial precursor tissue and/or a lens placode is formed in the surface layer of the cell aggregate in, for example, 10, 12, 14, 16, 18, 20, 22, 24, 26 or 28 days from the start of the suspension culture of the pluripotent stem cell aggregate. By selecting cell aggregates confirmed to have formed a corneal epithelial precursor tissue and/or a lens placode from the cultured plural cell aggregates, a cell aggregate containing a corneal epithelial precursor tissue and/or a lens placode, as well as a neural retinal tissue, wherein the corneal epithelial precursor tissue and/or the lens placode constitute(s) the surface layer of the cell aggregate, the neural retinal tissue is contained in the inside of the cell aggregate, and the corneal epithelial precursor tissue and/or the lens placode are(is) adjacent to the neural retinal tissue, can be obtained. As mentioned above, a population of cell aggregates containing a corneal precursor tissue at an efficiency of, for example, not less than 60%, preferably not less than 70%, more preferably not less than 80%, can be formed, and a population of cell aggregates containing a lens precursor tissue at an efficiency of, for example, not less than 10%, preferably not less than 15%, more preferably not less than 20%, can be obtained.

(7) Induction of Corneal Epithelium

The cell aggregate containing the corneal epithelial precursor tissue and the neural retinal tissue, which is obtained in the above-mentioned (6), wherein the corneal epithelial precursor tissue constitutes the surface layer of the cell aggregate, the neural retinal tissue is contained in the inside of the cell aggregate, and the corneal epithelial precursor tissue is adjacent to the neural retinal tissue is further cultured in suspension in a medium containing a bone morphogenic factor signal transduction pathway activating substance (BMP4 etc.), whereby further differentiation of the corneal epithelial precursor tissue into the corneal epithelium is induced. As a result, a cell aggregate containing the corneal epithelium and neural retinal tissue, wherein the corneal epithelium constitutes the surface layer of the cell aggregate, the neural retinal tissue is contained in the inside of the cell aggregate, and the corneal epithelium is adjacent to the neural retinal tissue can be formed. Induction of the corneal epithelium can be confirmed using expression of a corneal epithelium marker (e.g., cytokeratin 3, cytokeratin 12, cytokeratin 14, p63, ZO-1) and a corneal epithelium stem cell marker (e.g., cytokeratin 15) as an index. The period necessary for the induction of the corneal epithelium varies depending on the culture conditions, and the kind of a mammal from which the pluripotent stem cell is derived, and cannot be specified generally. However, when human pluripotent stem cells are used, a corneal epithelium is formed in the surface layer of the cell aggregate in, for example, 20, 25, 30, 35, 40, 45, 50, 55, 60, 65 or 70 days from the start of the floating culture of the pluripotent stem cell aggregate. By selecting a cell aggregate confirmed to have formed a corneal epithelium from the cultured plural cell aggregates, a cell aggregate containing a corneal epithelium and a neural retinal tissue, wherein the corneal epithelium constitutes the surface layer of the cell aggregate, the neural retinal tissue is contained in the inside of the cell aggregate, and the corneal epithelium is adjacent to the neural retinal tissue, can be obtained.

As a medium used for further suspension culture to induce further differentiation of a corneal epithelial precursor tissue into the corneal epithelium, a medium for suspension culture of pluripotent stem cell aggregates described in the above-mentioned (4) can be used continuously. As a basal medium, a medium modified to be suitable for the culture of the cells of corneal epithelium and epidermis epithelium may be adopted. Examples of such medium include, but are not limited to, CnT-30 medium (manufactured by CELLnTEC), Defined K-SFM medium (manufactured by Gibco/Invitrogen) and the like.

(8) Stratification of Corneal Epithelium

The cell aggregate containing the corneal epithelium and the neural retinal tissue, which is obtained in the above-mentioned (7), wherein the corneal epithelium constitutes the surface layer of the cell aggregate, the neural retinal tissue is contained in the inside of the cell aggregate, and the corneal epithelium is adjacent to the neural retinal tissue is further cultured in suspension in a medium containing a bone morphogenic factor signal transduction pathway activating substance (BMP4 etc.), whereby stratification of the corneal epithelium is induced. As a result, a cell aggregate containing the stratified corneal epithelium and neural retinal tissue, wherein the corneal epithelium constitutes the surface layer of the cell aggregate, and the neural retinal tissue is contained in the inside of the cell aggregate can be formed. Stratification of the corneal epithelium can be confirmed by microscopic observation of the stratified structure of the epithelium characteristic of the mature cornea, wherein the surface layer is squamous epithelium, and the deep layer is cuboidal epithelium. The period necessary for the stratification of the corneal epithelium varies depending on the culture conditions, and the kind of a mammal from which the pluripotent stem cell is derived, and cannot be specified generally. However, when human pluripotent stem cells are used, a stratified corneal epithelium is formed in the surface layer of the cell aggregate in, for example, 75, 80, 84, 90 or 95 days from the start of the suspension culture of the pluripotent stem cell aggregate. By selecting a cell aggregate confirmed to have formed a stratified corneal epithelium from the cultured plural cell aggregates, a cell aggregate containing a stratified corneal epithelium and a neural retinal tissue, wherein the corneal epithelium constitutes the surface layer of the cell aggregate, and the neural retinal tissue is contained in the inside of the cell aggregate, can be obtained.

As a medium used for further suspension culture to induce stratification of a corneal epithelium, a medium for suspension culture of pluripotent stem cell aggregates described in the above-mentioned (4) can be used continuously. As a basal medium, a medium modified to be suitable for the culture of the cells of corneal epithelium and epidermis epithelium may be adopted. Examples of such medium include, but are not limited to, CnT-30 medium (manufactured by CELLnTEC), Defined K-SFM medium (manufactured by Gibco/Invitrogen) and the like.

A medium used for further suspension culture may contain a fibroblast growth factor. That is, in one embodiment of the method of the present invention, the suspension culture of the cell aggregate is entirely or partially performed in the presence of a fibroblast growth factor. As the fibroblast growth factor, any substance having an activity to grow fibroblast can be used. Examples of the fibroblast growth factor include bFGF. While bFGF is mainly described in the following, the fibroblast growth factor used in the present invention is not limited to bFGF. Stratification of the corneal epithelium is promoted by the addition of a fibroblast growth factor (bFGF etc.).

bFGF is a known cytokine, and the amino acid sequence thereof is also known. bFGF to be used in the present invention is mammalian bFGF. Examples of the mammal include experiment animals such as rodents including mouse, rat, hamster, guinea pig and the like, rabbit and the like; domestic animals such as swine, bovine, goat, horse, sheep and the like; companion animals such as dog, cat and the like; and primates such as human, monkey, orangutan, chimpanzee and the like. bFGF is preferably bFGF of rodents (mouse, rat etc.) or primates (human etc.), most preferably human bFGF. Examples of the representative amino acid sequence of human bFGF include NCBI accession number NP 001997.5 (updated on Jul. 7, 2013) and the like.

When bFGF is used as a fibroblast growth factor, the concentration of the bFGF in the medium used for stratification of the corneal epithelium is not particularly limited as long as it promotes stratification of the corneal epithelium. However, it is generally about 0.1-1000 ng/ml, preferably about 0.5-500 ng/ml, more preferably about 2-200 ng/ml.

(9) Induction of Mesenchymal Tissue

The cell aggregate containing the corneal epithelium or a precursor tissue thereof and the neural retinal tissue, which is obtained in the above-mentioned (6) or (7), wherein the corneal epithelium or a precursor tissue thereof constitutes the surface layer of the cell aggregate, the neural retinal tissue is contained in the inside of the cell aggregate, and the corneal epithelium or a precursor tissue thereof is adjacent to the neural retinal tissue is further cultured in suspension in a medium containing a bone morphogenic factor signal transduction pathway activating substance (BMP4 etc.), whereby a mesenchymal tissue is formed between the corneal epithelium or a precursor tissue thereof, and the neural retinal tissue. The mesenchymal tissue exhibits the morphology of a layer wherein the mesenchymal cells are densely aggregated. It is known that the adult cornea comprises three layers of epithelium, stroma and endothelium from the surface toward the inside, and stroma and endothelium are developed from the mesenchymal cells rather than the surface ectoderm. That is, the present invention can reproduce, in a cell aggregate, the development of corneal stroma and corneal endothelium in the embryo in vivo. According to the results of further culture, the obtained cell aggregate contains the corneal epithelium (preferably, stratified corneal epithelium) or a precursor tissue thereof, a mesenchymal tissue, and a neural retinal tissue, wherein the corneal epithelium (preferably, stratified corneal epithelium) or a precursor tissue thereof, a mesenchymal tissue, and a neural retinal tissue are disposed in layers in the order of the corneal epithelium (preferably, stratified corneal epithelium) or a precursor tissue thereof, the mesenchymal tissue, and the neural retinal tissue from the surface layer of the cell aggregate toward the inside.

In one embodiment, the mesenchymal tissue formed between the corneal epithelium or a precursor tissue thereof, and the neural retinal tissue may be corneal stroma or a precursor tissue thereof, and corneal endothelium or a precursor tissue thereof. In this embodiment, the cell aggregate obtained as a result of further culture contains corneal epithelium (preferably, stratified corneal epithelium) or a precursor tissue thereof, corneal stroma or a precursor tissue thereof, corneal endothelium or a precursor tissue thereof, and a neural retinal tissue, wherein these are disposed in layers in the order of the corneal epithelium (preferably, stratified corneal epithelium) or a precursor tissue thereof, corneal stroma or a precursor tissue thereof, corneal endothelium or a precursor tissue thereof, and a neural retinal tissue from the surface layer of the cell aggregate toward the inside. That is, in the cell aggregate, cornea or a precursor tissue thereof (corneal like tissue) containing corneal epithelium (preferably, stratified corneal epithelium) or a precursor tissue thereof, corneal stroma or a precursor tissue thereof, and corneal endothelium or a precursor tissue thereof is formed adjacent to and on the outside of the neural retinal tissue.

Induction of a mesenchymal tissue, or corneal stroma or a precursor tissue thereof, and corneal endothelium or a precursor tissue thereof can be confirmed using expression of the markers of corneal stroma, corneal endothelium, or a precursor tissue thereof including PDGFR-α, Pitx2, ABCG2 and the like, or the morphological characteristic of being a layer wherein mesenchymal cells are densely aggregated as an index. Furthermore, since the corneal endothelium takes the morphology like an epithelized endothelial cell layer, it is possible to distinguish corneal stroma (or a precursor tissue thereof) from corneal endothelium (or a precursor tissue thereof) or confirm induction of corneal endothelium or a precursor tissue thereof, by using such morphological characteristic as an index.

The period necessary for the induction of the mesenchymal tissue (corneal stroma or a precursor tissue thereof, and corneal endothelium or a precursor tissue thereof) varies depending on the culture conditions, and the kind of a mammal from which the pluripotent stem cell is derived, and cannot be specified generally. However, when human pluripotent stem cells are used, a mesenchymal tissue (corneal stroma or a precursor tissue thereof, and corneal endothelium or a precursor tissue thereof) is formed between the corneal epithelium or a precursor tissue thereof, and the neural retinal tissue in, for example, 20, 25, 30, 35, 40, 45, 50, 55, 60, 65 or 70 days from the start of the suspension culture of the pluripotent stem cell aggregate. By selecting a cell aggregate confirmed to have formed a mesenchymal tissue (corneal stroma or a precursor tissue thereof, and corneal endothelium or a precursor tissue thereof), a cell aggregate containing corneal epithelium (preferably, stratified corneal epithelium) or a precursor tissue thereof, mesenchymal tissue (corneal stroma or a precursor tissue thereof, and corneal endothelium or a precursor tissue thereof), and a neural retinal tissue, in the above-mentioned embodiment, can be obtained.

As a medium used for further suspension culture to induce a mesenchymal tissue, a medium for suspension culture of pluripotent stem cell aggregates described in the above-mentioned (4) can be used continuously. As a basal medium, a medium modified to be suitable for the culture of the cells of corneal epithelium and epidermis epithelium may be adopted. Examples of such medium include, but are not limited to, CnT-30 medium (manufactured by CELLnTEC), Defined K-SFM medium (manufactured by Gibco/Invitrogen) and the like.

When formation of a cell aggregate in the above-mentioned embodiment, which contains stratified corneal epithelium, a mesenchymal tissue (corneal stroma or a precursor tissue thereof, and corneal endothelium or a precursor tissue thereof), and a neural retinal tissue is desired, a medium used for further suspension culture may contain a fibroblast growth factor (bFGF etc.).

When bFGF is used as a fibroblast growth factor, the concentration of bFGF in the medium used for further suspension culture is not particularly limited as long as it promotes stratification of the corneal epithelium. However, it is generally about 0.1-1000 ng/ml, preferably about 0.5-500 ng/ml, more preferably about 2-200 ng/ml.

(10) Induction of Lens Vesicle

The cell aggregate containing the lens placode and the neural retinal tissue, which is obtained in the above-mentioned (6), wherein the lens placode constitutes the surface layer of the cell aggregate, the neural retinal tissue is contained in the inside of the cell aggregate, and the lens placode is adjacent to the neural retinal tissue is further cultured in suspension in a medium containing a bone morphogenic factor signal transduction pathway activating substance (BMP4 etc.), whereby invagination of the lens placode is induced and a lens vesicle is formed. As a result, a cell aggregate containing a lens vesicle and a neural retinal tissue can be formed. Formation of a lens vesicle can be confirmed using a morphological characteristic of being a lens precursor tissue marker (e.g., L-Maf)-positive vesicle as an index. The period necessary for the formation of the lens vesicle varies depending on the culture conditions, and the kind of a mammal from which the pluripotent stem cell is derived, and cannot be specified generally. However, when human pluripotent stem cells are used, a lens vesicle is formed in, for example, 20, 25, 30, 35, 40, 45, 50, 55, 60, 65 or 70 days from the start of the suspension culture of the pluripotent stem cell aggregate. By selecting a cell aggregate confirmed to have formed a lens vesicle from the cultured plural cell aggregates, a cell aggregate containing a lens vesicle and cell aggregate neural retinal tissue can be obtained.

As a medium used for further suspension culture, a medium for suspension culture of pluripotent stem cell aggregates described in the above-mentioned (4), added with a fibroblast growth factor, can be used. That is, in one embodiment of the method of the present invention, the suspension culture of the cell aggregate is entirely or partially performed in the presence of a fibroblast growth factor. As the fibroblast growth factor, any substance having an activity to grow fibroblast can be used. Examples of the fibroblast growth factor include bFGF. While bFGF is mainly described in the following, the fibroblast growth factor used in the present invention is not limited to bFGF. By the addition of a fibroblast growth factor (bFGF etc.), the formed lens vesicle comes to show morphological polarity common with that observed in the development of a lens in vivo, in that it is thin in the part anterior to and thick in the part posterior to the anterior-posterior axis. While invagination of lens placode and formation of a lens vesicle can also be induced by continuously using a medium for floating culture of pluripotent stem cell aggregates, which is described in the above-mentioned (4), without adding a fibroblast growth factor (bFGF etc.), the above-mentioned tissue polarity does not appear clearly.

When bFGF is used as a fibroblast growth factor, the concentration of bFGF in the medium used for formation induction of lens vesicle is not particularly limited as long as it can impart the aforementioned morphological polarity to a lens vesicle. However, it is generally about 0.1-1000 ng/ml, preferably about 0.5-500 ng/ml, more preferably about 2-200 ng/ml.

(11) Production of Anterior Eye Segment Tissue or Partial Structure Thereof, or Precursor Tissue Thereof In a further aspect, an anterior eye segment tissue or a partial structure thereof, or a precursor tissue thereof can be separated from a cell aggregate obtained as mentioned above. In one embodiment, an anterior eye segment tissue or a partial structure thereof, or a precursor tissue thereof can be separated together with the neural retinal tissue. Furthermore, the present invention provides a cell aggregate, an anterior eye segment tissue or a partial structure thereof, or a precursor tissue thereof obtained by the above-mentioned method. For example, a surface layer containing the cornea or a precursor tissue thereof can be isolated from a cell aggregate containing the cornea or a precursor tissue thereof and a neural retinal tissue, wherein the cornea or a precursor tissue thereof constitutes the surface layer of the cell aggregate, the neural retinal tissue is contained in the inside of the cell aggregate, and the cornea or a precursor tissue thereof is adjacent to the neural retinal tissue. In the cell aggregate obtained in the above-mentioned (8), since the cornea or a precursor tissue thereof forms a layer separable by hand in the surface layer of the aggregate, the cornea or a precursor tissue thereof can be isolated easily without an enzyme treatment and the like. Furthermore, by dispersing the obtained cornea or a precursor tissue thereof with an enzyme and the like, corneal cells and corneal progenitor cells can be separated with high purity even without using FACS and the like. The thus-obtained cornea or a precursor tissue thereof can be used for transplantation as it is or in the form of a sheet by culture.

In this way, an anterior eye segment tissue or a partial structure thereof, or a precursor tissue thereof obtained by the present invention can be used for transplantation. For example, an anterior eye segment tissue or a partial structure thereof, or a precursor tissue thereof obtained by the present invention can be used as a therapeutic drug for diseases resulting from the disorders of anterior eye segment tissues, or for supplementing tissues for the damaged anterior eye segment tissues. By transplanting an anterior eye segment tissue or a partial structure thereof, or a precursor tissue thereof obtained by the present invention to patients with diseases resulting from the disorders of anterior eye segment tissues or damaged anterior eye segment tissues, the diseases resulting from the disorders of anterior eye segment tissues or damage on the anterior eye segment tissues can be treated. Examples of the diseases resulting from the disorders of anterior eye segment tissues include the diseases resulting from the disorders of the cornea (e.g., keratoconus, bullous keratopathy, corneal leukoma, herpescornea, corneal dystrophy, corneal damage due to failure of laser surgery of myopia such as LASEK, PRK and the like), diseases resulting from the disorders of lens (e.g., congenital cataract, acquired cataract) and the like.

In transplantation therapy, graft rejection due to the difference in the histocompatibility antigen is often problematic, which problem, however, can be solved by using a pluripotent stem cell (e.g., induced pluripotent stem cell) established from the somatic cell of the transplantation recipient. That is, in a preferable embodiment, a pluripotent stem cell (e.g., induced pluripotent stem cell) established from the somatic cell of the recipient is used as a pluripotent stem cell in the method of the present invention, and an anterior eye segment tissue or a partial structure thereof, or a precursor tissue thereof, which is immunologically self for the recipient, is produced and transplanted to the recipient.

Furthermore, an anterior eye segment tissue or a partial structure thereof, or a precursor tissue thereof, which is obtained by the present invention, can be used for screening and evaluation of drugs. Particularly, since an anterior eye segment tissue or a partial structure thereof, or a precursor tissue thereof, which is obtained by the present invention, has a higher structure extremely similar to that of an anterior eye segment tissue or a precursor tissue thereof in the living organisms, as evidenced by adjoining steric formation of retina, lens and cornea, and a corneal precursor tissue having each precursor tissue of corneal epithelium (preferably stratified corneal epithelium), corneal stroma and corneal endothelium in the form of a layer, it can be applied to screening for a therapeutic drug for diseases resulting from disorders of anterior eye segment tissues, and damaged anterior eye segment tissues, side effects and toxicity tests (e.g., substituting test of cornea stimulation test) of pharmaceutical products and cosmetics, and the development of a new therapeutic method for diseases of anterior eye segment tissue and the like.

The present invention is explained in more detail in the following by referring to the following Examples, which are mere exemplifications and do not limit the scope of the present invention.

EXAMPLES

Example 1: Self-Organization of Lens and Corneal Precursor Tissue by Suspension Aggregate Culture of Human ES Cells (Method)

Human ES cells (KhES-1; a fluorescence protein gene Venus is knocked-in a retina specific gene Rx) were dispersed to single cells by a trypsin treatment, and according to the SFEBq method (Nakano et al, Cell StemCell, 10(6): 771-785, 2012), aggregates were formed and subjected to suspension aggregate culture at 37° C. in the presence of 5% $CO_2$ for differentiation induction. The dispersed 5000 human ES cells were seeded in each well of a V bottom 96 well plate applied with a low cell adsorptive surface coating, and a chemically synthesized medium free of a growth factor (growth-factor-free Chemically Defined Medium; gfCDM; Wataya et al, Proc Natl Acad Sci USA, 105(33): 11796-11801, 2008) added with 5% KSR (Knockout Serum Replacement) was used as a culture medium for differentiation induction. To suppress dispersion-induced cell death, 20 μM of a ROCK inhibitor Y-27632 was added for the first 3 days of differentiation induction, and the concentration thereof was reduced to half for the next 3 days. From day 3 to day 18 after the start of the differentiation induction, 5 nM of BMP4 was added, and the concentration thereof was reduced to half from day 18 to day 21. These aggregates were analyzed by immunohistostaining.

(Results)

From day 9 from the start of the differentiation induction, strong fluorescence of Rx::venus was observed in the inside of the aggregate. On day 12 from the start of the differentiation induction, the fluorescence was observed irrespective of the presence or absence of the addition of BMP4, and became about 2 times or more stronger by a BMP4 treatment.

Figure 1B:
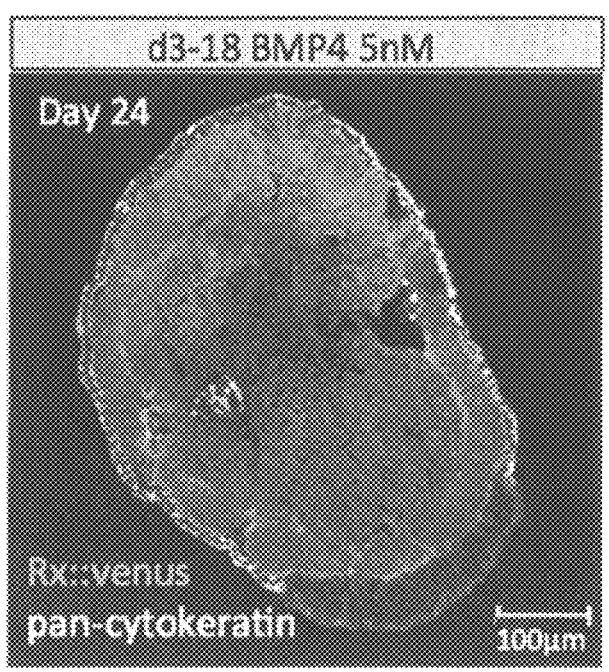
FIG. 1B shows that the epithelial cell layer formed in the surface layer of human ES cell aggregate (day 24) obtained by the SFEBq method under BMP4 addition conditions is pan-cytokeratin positive.
Figure 1C:
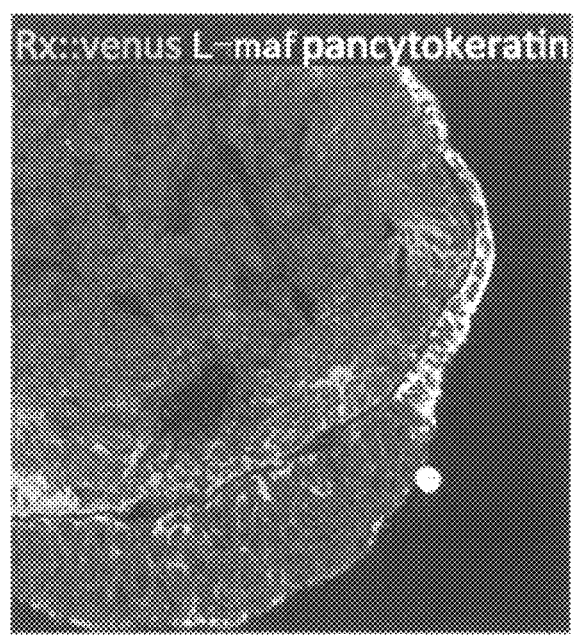
FIG. 1C shows that L-Maf positive lens placode-like tissue where the epithelial cell layer is thickened is formed in the surface layer of human ES cell aggregate (day 24) obtained by the SFEBq method under BMP4 addition conditions.

The Rx::venus positive tissue showed a neuroepithelium-like structure (pseudostratified columnar epithelium), expressed neural retinal marker Chx10 and was found to have formed neural retina. On day 14 from the start of the differentiation induction, formation of an Rx::venus negative epithelial cell layer different from the neural retina was observed in the surface layer of the aggregate (FIG. 1A). On day 24 from the start of the differentiation induction, the epithelial cell layer in the surface tested positive to Pan-cytokeratin and positive to E-cadherin which are a nonneural ectodermal epithelial markers (FIG. 1B). Such self-organization of a nonneural ectodermal epithelial tissue on the outside of the neural retina was observed with good reproducibility in not less than 90% of the aggregates. It was suggested that the epithelial cell layer in the surface was highly or moderately thickened (placode formation), and each formed lens placode or a corneal epithelial precursor tissue. The lens placode-like tissue was positive to L-Maf, which is a lens precursor tissue marker (FIG. 10). The corneal epithelial precursor tissue was formed in not less than 90% of the aggregates, and the lens placode was formed in 50% of the aggregates.

Example 2: Expression of Corneal Marker by Long-Term Culture of Corneal Precursor Tissue Self-Organized from Human ES Cells (Method)

After culture in a V bottom 96 well plate under culture conditions of Example 1 up to day 18 of differentiation induction, suspended aggregates were transferred to a cell nonadsorptive petri dish (diameter 6 cm), and suspension culture was performed at 37° C. in the presence of 5% $CO_2$, 40% $O_2$. The culture medium used for the culture was gfCDM+5% KSR added with 1 nM BMP4 from days 18 to 30, and any of the following two media (based on commercially available medium known to support culture of corneal epithelium and epidermis epithelial) from day 30 ff., followed by analysis by immunohistostaining on day 55.
1) culture medium of CnT-30 medium (CELLnTEC) added with 1 nM BMP4
2) culture medium of defined K-SFM medium (Gibco/Invitrogen) added with 10% FBS and 1 nM BMP4

(Results)

Figure 2:
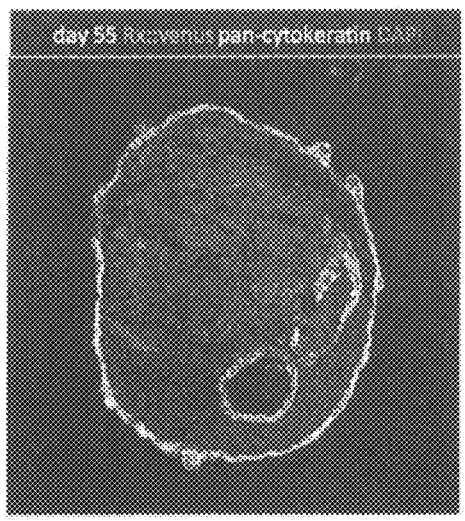
FIG. 2 shows that the epithelial tissue formed in the surface layer of human ES cell aggregate (day 55) obtained by the SFEBq method under BMP4 addition conditions expresses cytokeratin 3 (CK3), cytokeratin 12 (CK12) and cytokeratin 14 (CK14), which are characteristic of corneal epithelium.
Figure 2:
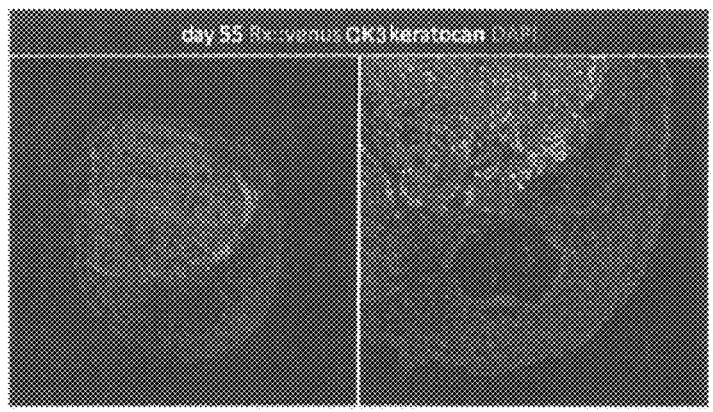
Figure 2:
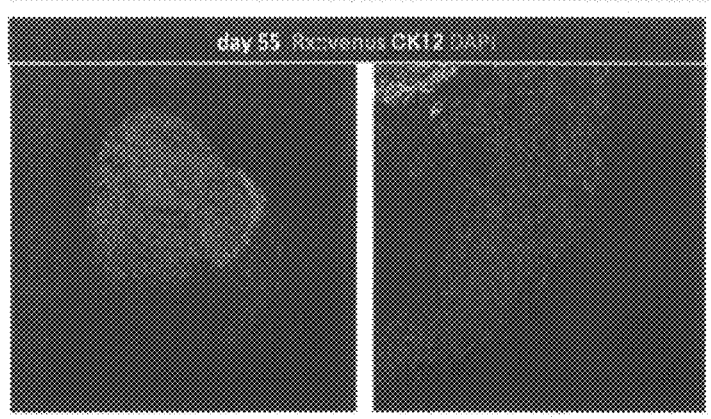
Figure 2:
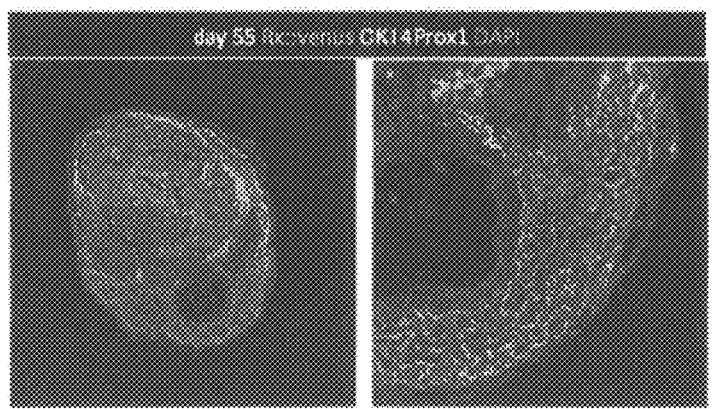

In a culture using the culture medium of any of the above-mentioned 1) and 2), the epithelial precursor tissue self-organized in the surface layer of the human ES cell aggregate permitted expansion culture and, on 55 days after the start of the differentiation culture, formation of an epithelial structure expressing cytokeratin 3 (CK3), cytokeratin 12 (CK12), cytokeratin 14 (CK14), p63, and ZO-1, which are specific to corneal epithelium, was observed in addition to being positive to Pan-cytokeratin, in not less than 80% of the aggregates (FIG. 2). The results have clearly demonstrated that the epithelial tissue in the surface layer, which was sterically formed by the self-organization by the method of the present invention, is a precursor tissue of the cornea.

Example 3: Self-Organization of Corneal Precursor Tissue Having Both Epithelial Tissue and Mesenchymal Tissue from Human ES Cells (Method)

In the same manner as in Example 2, culture was performed up to day 30. That is, human ES cell aggregates were cultured in a V bottom 96 well plate under culture conditions of Example 1 up to day 18 of differentiation induction, then suspended aggregates were transferred to a cell nonadsorptive petri dish (diameter 6 cm), and suspension culture was performed at 37° C. in the presence of 5% $CO_2$, 40% $O_2$. The culture medium used for the culture was gfCDM+5% KSR added with 1 nM BMP4 from days 18 to 30, followed by analysis by immunohistostaining. A part of the cultured aggregates was continuously subjected to suspension culture after day 30 up to day 55. For the latter culture, a culture medium of defined K-SFM medium (Gibco/Invitrogen) added with 10% FBS and 1 nM BMP4 was used.

(Results)

Figure 3A:
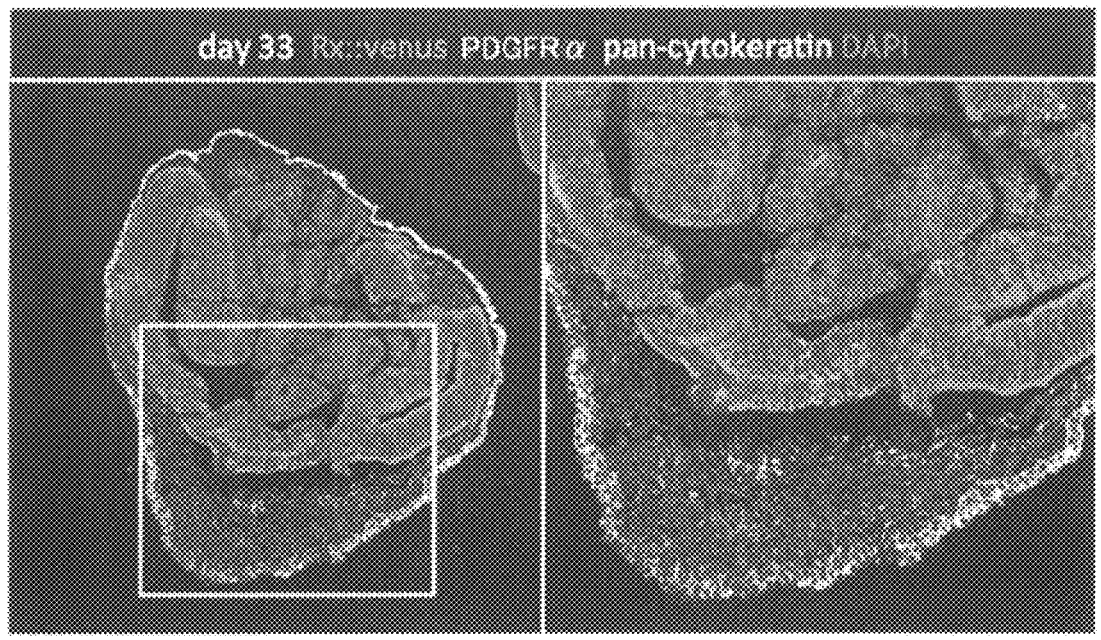
FIG. 3A shows expression of PDGFR-alpha in a mesenchymal cell aggregate layer between the thickened corneal epithelium and neural retinal tissue in the surface layer of human ES cell aggregate (day 33) obtained by the SFEBq method under BMP4 addition conditions.
Figure 3B:
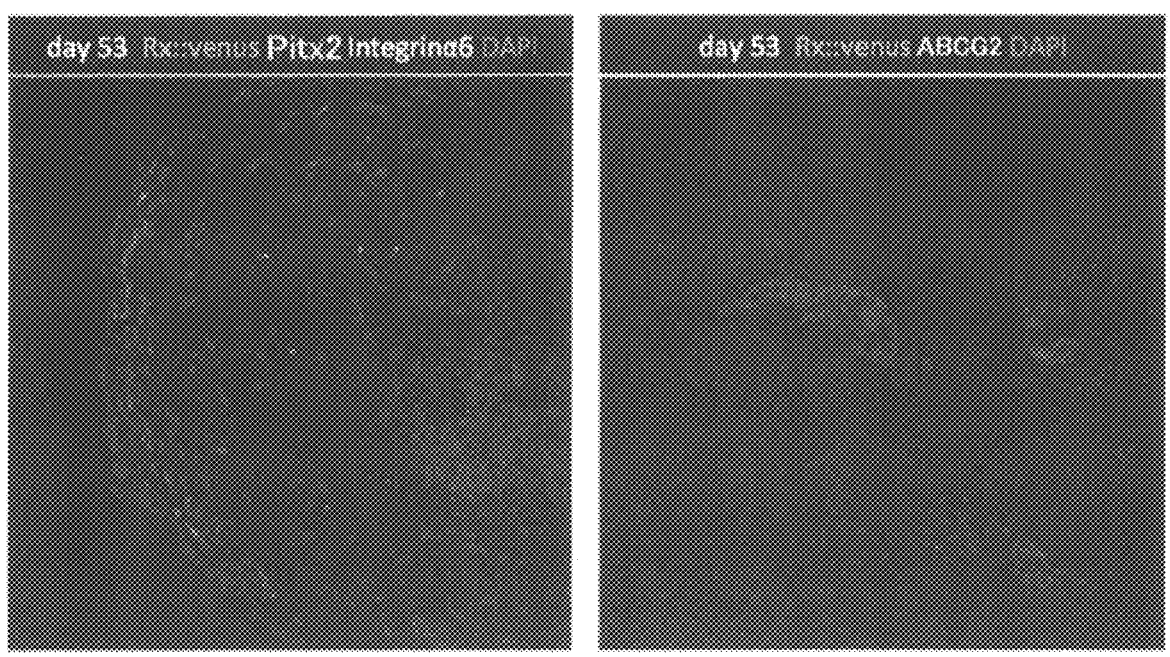
FIG. 3B shows expression of Pitx2 and ABCG2 in a mesenchymal cell aggregate layer between the thickened corneal epithelium and neural retinal tissue in the surface layer of human ES cell aggregate (day 53) obtained by the SFEBq method under BMP4 addition conditions.
Figure 3C:
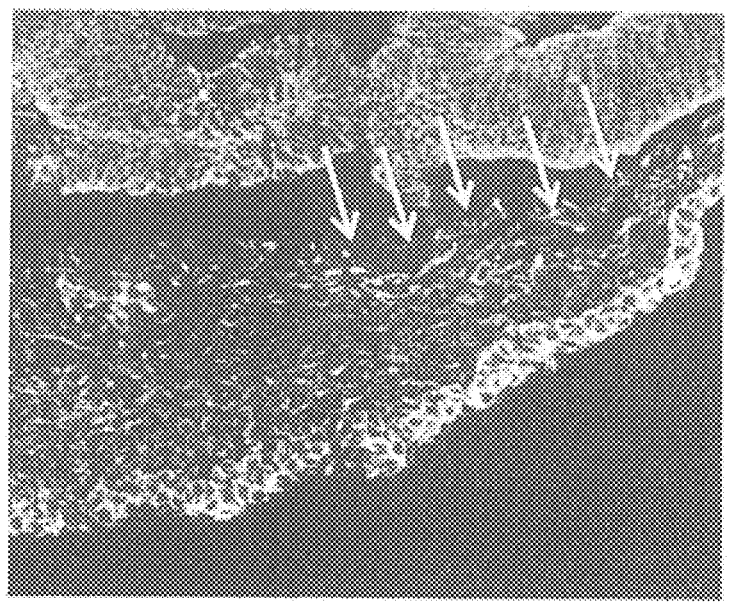
FIG. 3C shows the morphology of an epithelized endothelial cell layer formed in the innermost part of the mesenchymal cell aggregate layer.

As described in Examples 1 and 2, human ES cell aggregates have corneal epithelium and lens tissue derived from surface ectoderm in the surface layer, and a neural retinal tissue in the inside. In the sample on day 30, mesenchymal cells were present immediately below moderately thickened corneal epithelium (i.e., between corneal epithelium and neural retinal tissue) to form a densely coagulated layer, which was confirmed in 70% of the aggregates. The mesenchymal cells were positive for a mesenchymal marker PDGFR-alpha (day 30; FIG. 3A), and also positive for Pitx2 and ABCG2 expressed in the mesenchymal cell (derived from neural crest cell) of the initial cornea (day 53; FIG. 3B). In the cornea in the living body, corneal stroma is present beneath the corneal epithelium layer in the surface, and corneal endothelium is present beneath the corneal stroma, and corneal stroma and corneal endothelium are derived from the mesenchymal cells derived from the neural crest cells that aggregate under the corneal epithelium. Such state similar to that in the living body could be induced in the surface layer of human ES cell aggregates and the layer therebeneath. Furthermore, the innermost part of the aggregate layer of mesenchymal cells was partly epithelized, which suggested morphological formation of an endothelium-like cell layer (FIG. 3C, arrow). Thus, it was shown that not only a corneal epithelial tissue is formed, but a precursor tissue of the whole corneal layer containing corneal stroma and corneal endothelium can be sterically formed from human pluripotent stem cells in the self-organization of the anterior eye segment by the method of the present invention.

Example 4: Self-Organization of Crystalline Lens Vesicle from Lens Placode Derived from Human ES Cells (Method)

Under the conditions of Example 3, suspension culture of human ES cell aggregates was continued up to day 30 from the start of the differentiation induction. In this case, 20 ng/ml bFGF was added to the medium from day 15. As other culture conditions, after culture for 30 days under conditions of Example 3, culture was performed in gfCDM+10% KSR or GMEM+10% KSR from days 30 to 55.
(Results)

Figure 4A:
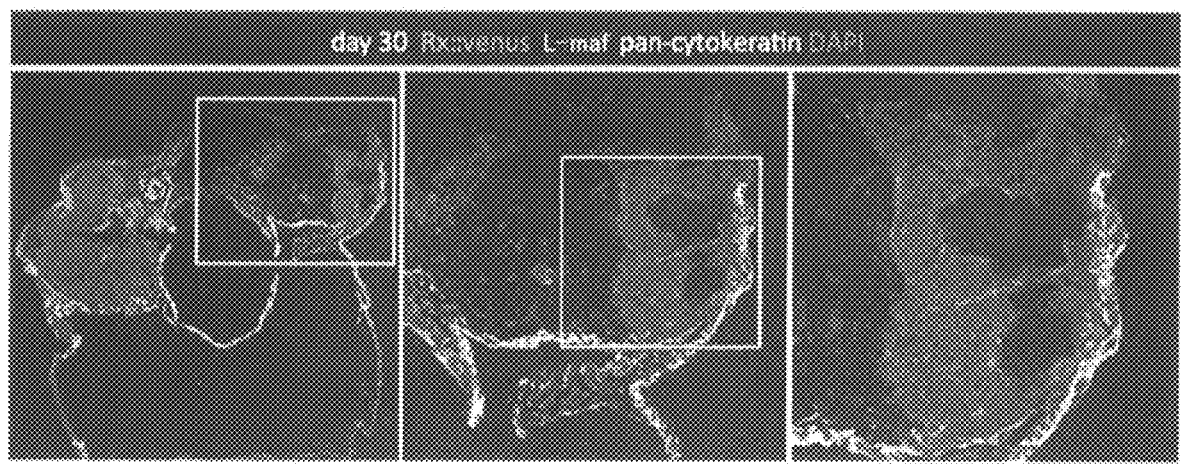
FIG. 4A shows a lens vesicle-like vesicle observed in the bFGF addition group, in which formation of a lens tissue having morphological polarity (thin in the anterior part and thick in the posterior part) along the anterior-posterior axis, which is seen in the development of lens in vivo, is observed.
Figure 4B:
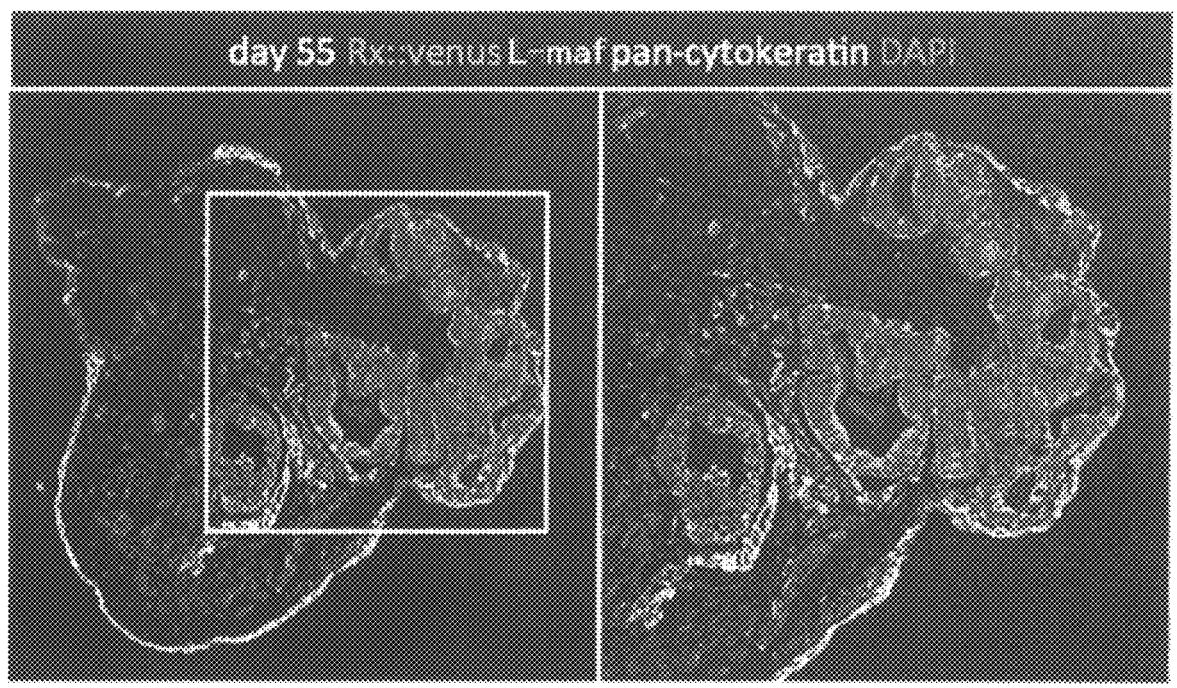
FIG. 4B shows a lens vesicle-like vesicle observed in the bFGF non-addition group. The tissue polarity observed in the bFGF addition group is not clear.

In the sample on day 30, irrespective of the presence or absence of the addition of bFGF, a lens vesicle-like vesicle was formed by invagination from the lens placode in the surface layer in 40% of aggregates. This vesicle was positive for a lens initial marker L-Maf, and the expression level thereof increased twice or more by the addition of bFGF. In the addition example of bFGF, morphological polarity (formation of lens tissue thinner in the anterior and thicker in the posterior), which is observed along the anterior-posterior axis in the development of a lens in vivo, was seen in a lens vesicle-like vesicle, and lens formation closer to that in vivo was confirmed (FIG. 4A). While invagination and formation of a lens vesicle-like vesicle was observed with good reproducibility even when cultured in gfCDM+10% KSR or GMEM+10% KSR up to day 55 in the absence of bFGF, the above-mentioned tissue polarity does not appear clearly (FIG. 4B). Therefore, it was suggested that the polarity formation was not merely caused by an accelerated development by bFGF, but qualitative promotion of the development program toward maturation of a lens.

Example 5: Self-Organization of Stratified Corneal Epithelium (Method)

Human ES cell aggregates were cultured in a V bottom 96 well plate under the same conditions as in the above-mentioned Examples up to day 30 of differentiation induction. Thereafter, suspended aggregates were transferred to a cell nonadsorptive petri dish (diameter 6 cm), and suspension culture was performed under the conditions of 37° C., 5% $CO_2$, 40% $O_2$. As the culture medium, gfCDM+5% KSR was used up to day 30, and gfCDM+20% KSR was used from day 30. From days 3 to 18, 5 nM BMP4 was added. On day 24, the BMP4 concentration was reduced to half (2.5 nM), and continuously added at 1 nM from day 30. In addition, basic FGF was added to the medium at a concentration of 20 ng/ml from day 15 during culture. The suspended aggregates were analyzed by immunohistostaining on day 84.
(Results)

Figure 5A:
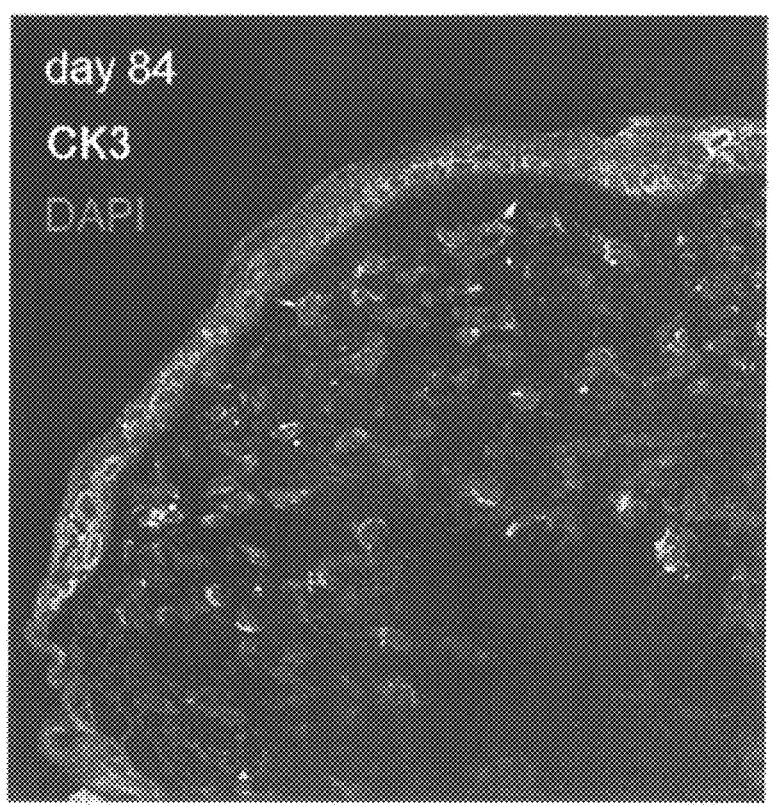
FIG. 5A shows expression of CK3 in stratified corneal epithelium.
Figure 5B:
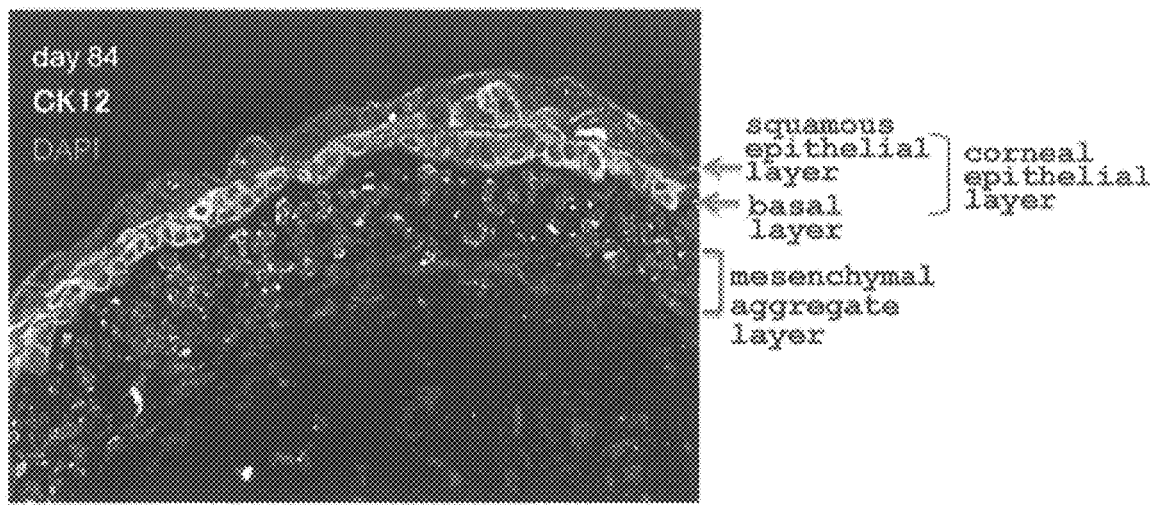
FIG. 5B shows expression of CK12 in stratified corneal epithelium.
Figure 5C:
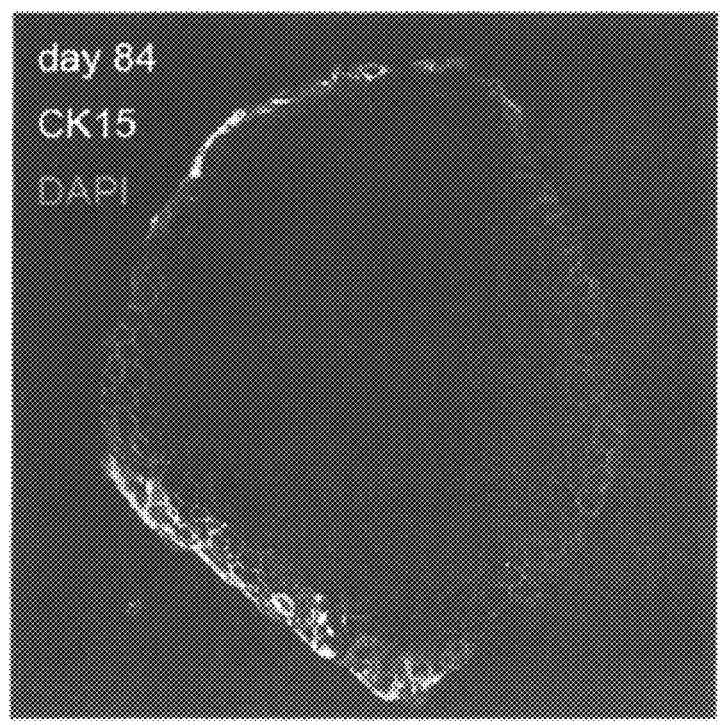
FIG. 5C shows expression of CK15 in stratified corneal epithelium.
Figure 5D:
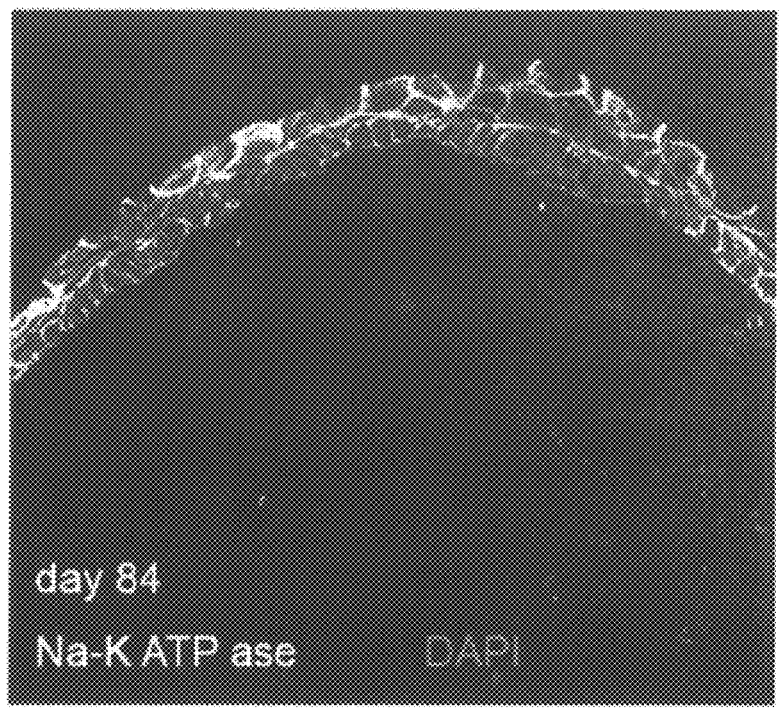
FIG. 5D shows expression of Na—K ATPase in stratified corneal epithelium.

An epithelial precursor tissue self-organized in the surface layer of the human ES cell aggregate was found, and on 84 days after the start of the differentiation culture, corneal epithelium positive to cytokeratin 3 (CK3) specific to corneal epithelium, cytokeratin 12 (CK12), cytokeratin 15 (CK15) which is a marker of corneal epithelium stem cell was found (FIGS. 5A, 5B and 5C). In addition, Na—K ATPase expressed on the corneal epithelium was also stained (FIG. 5D). The epithelium had a layered structure of the epithelium, which is characteristic of mature cornea, wherein the surface layer is squamous epithelium, and the deep layer is cuboidal epithelium (FIG. 5B). The results suggest the steric corneal epithelial precursor tissue formed by self-organization by the method of the present invention spontaneously performs stratification when it is matured further, and shows tissue construction inherent to the corneal epithelium and protein expression, which are close to those in the living body. Also, a mesenchymal aggregate layer was found below the corneal epithelium, which clearly demonstrates that they are precursor tissues of the total corneal layers of epithelium, stroma and endothelium.

INDUSTRIAL APPLICABILITY

According to the present invention, anterior eye segment tissues such as lens, cornea and the like or a partial structure thereof, or a precursor tissue thereof can be sterically formed from pluripotent stem cells under floating culture capable of affording a high-throughput. Therefore, the present invention is useful for practice of regenerative medicine in the ophthalmic field.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

This application is based on a patent application No. 2013-163586 filed in Japan (filing date: Aug. 6, 2013), the contents of which are incorporated in full herein.

The invention claimed is:

1. A production method of a cell aggregate comprising an anterior eye segment tissue or a partial structure thereof, or a precursor tissue thereof, comprising
    (a) culturing dispersed pluripotent stem cells in suspension in a serum-free medium to form an aggregate,
    (b) culturing the aggregate formed in step (a) in suspension in the absence of a substance that activates the pathway through which signals are transmitted upon binding of bone morphogenic protein 4 (BMP4) and a receptor,
    (c-1) culturing the aggregate cultured in step (b) in suspension in a medium in the presence of a substance that activates the pathway through which signals are transmitted upon binding of BMP4 and a receptor, to form (i) an Rx-positive and Chx10-positive neuroepithelium-like structure in the inside of the aggregate and (ii) an Rx-negative ectodermal epithelial cell layer on the surface of the aggregate, and
    (c-2) culturing the aggregate cultured in step (c-1) in suspension in a medium in the presence of a substance that activates the pathway through which signals are transmitted upon binding of BMP4 and a receptor in a concentration reduced to half or less than that in step (c-1) to form (iii) a corneal epithelial precursor tissue that is pan-cytokeratin positive, (iv) a lens placode that is L-Maf positive, or (v) both a corneal epithelial precursor tissue that is pan-cytokeratin positive and a lens placode that is L-Maf positive on the surface of the aggregate,
    wherein the medium in steps (c-1) and (c-2) is free of an Shh signal promoter, and
    wherein the suspension culture in steps (a), (b), (c-1), and (c-2) is performed in the absence of a feeder cell.

2. The production method according to claim 1, wherein the suspension culture is performed entirely or partially in the presence of a fibroblast growth factor.

3. The method according to claim 1, wherein the pluripotent stem cells are embryonic stem cells or induced pluripotent stem cells.

4. The method according to claim 1, wherein the pluripotent stem cells are derived from human.

5. The method according to claim 1, wherein the cell aggregate further comprises a neural retinal tissue.

6. The method according to claim 1, wherein the anterior eye segment tissue is cornea and/or lens.

7. The method according to claim 1, wherein the cell aggregate comprises corneal epithelium as a partial structure of the anterior eye segment tissue, and further comprises a mesenchymal tissue, or corneal stroma and/or corneal endothelium derived therefrom.

8. The method according to claim 7, wherein the corneal epithelium is stratified.

9. The method according to claim 1, further comprising separating the anterior eye segment tissue or partial structure thereof or precursor tissue thereof from the cell aggregate.

10. The method according to claim 9, wherein the anterior eye segment tissue or partial structure thereof, or precursor tissue thereof is separated together with a neural retinal tissue.

11. The method according to claim 1, further comprising
(d) culturing the aggregate obtained in step (c-2) in suspension, until a corneal epithelium is induced from the corneal epithelial precursor tissue, in a medium in the presence of a substance that activates the pathway through which signals are transmitted upon binding of BMP4 and a receptor, wherein the medium is free of an Shh signal promoter.

12. The method according to claim 1, further comprising
(d) culturing the aggregate obtained in step (c-2) in suspension, until a mesenchymal tissue is formed in the aggregate, in a medium in the presence of a substance that activates the pathway through which signals are transmitted upon binding of BMP4 and a receptor, wherein the medium is free of an Shh signal promoter.

13. The method according to claim 1, further comprising
(d) culturing the aggregate obtained in step (c-2) in suspension, until a lens vesicle is formed in the aggregate, in a medium in the presence of a substance that activates the pathway through which signals are transmitted upon binding of BMP4 and a receptor, wherein the medium is free of an Shh signal promoter.

14. The method according to claim 1, wherein the substance that activates the pathway through which signals are transmitted upon binding of BMP4 and a receptor is BMP4.

15. The method according to claim 14, wherein BMP4 in step (c-1) has a concentration of 1-5 nM.

16. The method according to claim 1, wherein the suspension culture in step (c-2) is performed in the presence of 40% $O_2$.

17. A production method of a cell aggregate comprising a corneal epithelium constituting the surface layer of the cell aggregate, and a neural retinal tissue inside of the cell aggregate, comprising
(a) culturing dispersed pluripotent stem cells in suspension in a serum-free medium to form an aggregate,
(b) culturing the aggregate formed in step (a) in suspension in the absence of a substance that activates the pathway through which signals are transmitted upon binding of bone morphogenic protein 4 (BMP4) and a receptor,
(c-1) culturing the aggregate cultured in step (b) in suspension in a medium in the presence of a substance that activates the pathway through which signals are transmitted upon binding of BMP4 and a receptor, to form (i) an Rx-positive and Chx10-positive neuroepithelium-like structure in the inside of the aggregate and (ii) an Rx-negative ectodermal epithelial cell layer on the surface of the aggregate,
(c-2) culturing the aggregate cultured in step (c-1) in suspension in a medium in the presence of a substance that activates the pathway through which signals are transmitted upon binding of BMP4 and a receptor in a concentration reduced to half or less than that in step (c-1) to form (iii) a corneal epithelial precursor tissue that is pan-cytokeratin positive or (v) both a corneal epithelial precursor tissue that is pan-cytokeratin positive and a lens placode that is L-Maf positive on the surface of the aggregate, and
(d) culturing the aggregate obtained in step (c-2) in suspension in a medium in the presence of a substance that activates the pathway through which signals are transmitted upon binding of BMP4 and a receptor in a concentration reduced to half or less than that in step (c-1) to induce a corneal epithelium from the corneal epithelial precursor tissue, thereby obtaining a cell aggregate comprising a corneal epithelium constituting the surface layer of the cell aggregate, and a neural retinal tissue in the inside of the cell aggregate;
wherein the medium in steps (c-1), (c-2), and (d) is free of an Shh signal promoter, and
wherein the suspension culture in steps (a), (b), (c-1), (c-2), and (d) is performed in the absence of a feeder cell.

* * * * *